(12) United States Patent
Sershen et al.

(10) Patent No.: US 9,289,449 B2
(45) Date of Patent: Mar. 22, 2016

(54) HYDROGEL COMPOSITIONS

(71) Applicant: SpotLight Technology Partners LLC, Los Altos, CA (US)

(72) Inventors: Scott Robert Sershen, Foster City, CA (US); Suresh Subraya Pai, Los Altos, CA (US); Glen Gong, San Carlos, CA (US)

(73) Assignee: SpotLight Technology Partners LLC, Los Altos, CA (US)

( * ) Notice: Subject to any disclaimer, the term of this patent is extended or adjusted under 35 U.S.C. 154(b) by 0 days.

(21) Appl. No.: 14/339,336

(22) Filed: Jul. 23, 2014

(65) Prior Publication Data

US 2015/0011504 A1 Jan. 8, 2015

Related U.S. Application Data

(63) Continuation of application No. 13/505,684, filed as application No. PCT/US2010/055716 on Nov. 5, 2010, now Pat. No. 8,795,727.

(60) Provisional application No. 61/259,566, filed on Nov. 9, 2009.

(51) Int. Cl.
*A61K 9/14* (2006.01)
*A61K 31/722* (2006.01)
(Continued)

(52) U.S. Cl.
CPC .................. *A61K 31/722* (2013.01); *A61K 9/06* (2013.01); *A61K 9/146* (2013.01); *A61K 31/225* (2013.01); *A61K 47/34* (2013.01); *A61K 47/36* (2013.01); *A61L 24/0031* (2013.01); *A61L 24/08* (2013.01); *A61L 26/008* (2013.01); *A61L 26/0023* (2013.01); *A61L 27/20* (2013.01); *A61L 27/52* (2013.01); *A61L 31/042* (2013.01); *A61L 31/145* (2013.01); *C08J 3/075* (2013.01);
(Continued)

(58) Field of Classification Search
CPC ........................................................ A61K 9/06
See application file for complete search history.

(56) References Cited

U.S. PATENT DOCUMENTS

| 3,947,401 A | 3/1976 | Stamberger |
| 4,016,106 A | 4/1977 | Sawyer et al. |

(Continued)

FOREIGN PATENT DOCUMENTS

| JP | 2003-503367 | 1/2003 |
| JP | 2005-143920 | 6/2005 |

(Continued)

OTHER PUBLICATIONS

Chen et al. (2004) "Synthesis and pH sensitivity of carboxymethyl chitosan-based polyampholyte hydrogels for protein carrier matrices" Biomaterials 25:3725-3732.

(Continued)

*Primary Examiner* — Paul Dickinson
(74) *Attorney, Agent, or Firm* — Edward J. Baba; Khin K. Chin; Bozicevic, Field & Francis LLP

(57) ABSTRACT

Fragmented polysaccharide based hydrogel compositions and methods of making and using the same are provided. The subject polysaccharide based hydrogel compositions are prepared by combining a polysaccharide component with a hydrophilic polymer and a cross-linking agent. Also provided are kits and systems for use in preparing the subject compositions.

18 Claims, 4 Drawing Sheets

(51) Int. Cl.

| | | |
|---|---|---|
| *A61K 9/06* | (2006.01) | |
| *A61K 47/34* | (2006.01) | |
| *A61K 47/36* | (2006.01) | |
| *A61L 24/00* | (2006.01) | |
| *A61L 24/08* | (2006.01) | |
| *A61L 26/00* | (2006.01) | |
| *A61L 27/20* | (2006.01) | |
| *A61L 27/52* | (2006.01) | |
| *A61L 31/04* | (2006.01) | |
| *A61L 31/14* | (2006.01) | |
| *C08J 3/075* | (2006.01) | |
| *C08J 3/12* | (2006.01) | |
| *A61K 31/225* | (2006.01) | |
| *C08K 5/06* | (2006.01) | |
| *C09D 105/08* | (2006.01) | |

(52) U.S. Cl.
CPC .. *C08J 3/12* (2013.01); *C08K 5/06* (2013.01); *C09D 105/08* (2013.01); *C08J 2371/02* (2013.01); *C08J 2405/08* (2013.01)

(56) References Cited

U.S. PATENT DOCUMENTS

| | | | |
|---|---|---|---|
| 4,134,871 A | 1/1979 | Otani et al. | |
| 4,200,098 A | 4/1980 | Ayer et al. | |
| 4,273,734 A | 6/1981 | Seiderman | |
| 4,279,795 A | 7/1981 | Yamashita et al. | |
| 4,285,987 A | 8/1981 | Ayer et al. | |
| 4,359,558 A | 11/1982 | Gould et al. | |
| 4,408,023 A | 10/1983 | Gould et al. | |
| 4,434,153 A | 2/1984 | Urquhart et al. | |
| 4,439,583 A | 3/1984 | Gould et al. | |
| 4,439,584 A | 3/1984 | Gould et al. | |
| 4,439,585 A | 3/1984 | Gould et al. | |
| 4,485,089 A | 11/1984 | Leipold | |
| 4,526,938 A | 7/1985 | Churchill et al. | |
| 4,532,134 A | 7/1985 | Malette et al. | |
| 4,542,176 A | 9/1985 | Graham | |
| 4,549,952 A | 10/1985 | Columbus | |
| 4,570,629 A | 2/1986 | Widra | |
| 4,587,284 A | 5/1986 | Luissi et al. | |
| 4,589,226 A | 5/1986 | Stensaas | |
| 4,595,583 A | 6/1986 | Eckenhoff et al. | |
| 4,632,826 A | 12/1986 | Ploger et al. | |
| 4,642,233 A | 2/1987 | Urquhart et al. | |
| 4,657,553 A | 4/1987 | Taylor | |
| 4,663,149 A | 5/1987 | Eckenhoff et al. | |
| 4,673,566 A | 6/1987 | Goosen et al. | |
| 4,675,174 A | 6/1987 | Eckenhoff | |
| 4,681,582 A | 7/1987 | Yamamoto | |
| 4,683,092 A | 7/1987 | Tsang | |
| 4,689,293 A | 8/1987 | Goosen et al. | |
| 4,715,143 A | 12/1987 | Redenbaugh et al. | |
| 4,731,384 A | 3/1988 | Dell et al. | |
| 4,747,847 A | 5/1988 | Magruder et al. | |
| 4,772,474 A | 9/1988 | Eckenhoff et al. | |
| 4,781,714 A | 11/1988 | Eckenhoff et al. | |
| 4,795,590 A | 1/1989 | Kent et al. | |
| 4,802,997 A | 2/1989 | Fox et al. | |
| 4,806,355 A | 2/1989 | Goosen et al. | |
| 4,814,182 A | 3/1989 | Graham et al. | |
| 4,836,928 A | 6/1989 | Aoyagi et al. | |
| 4,842,867 A | 6/1989 | Ayer et al. | |
| 4,844,984 A | 7/1989 | Eckenhoff et al. | |
| 4,849,343 A | 7/1989 | Krull et al. | |
| 4,865,552 A | 9/1989 | Maloney et al. | |
| 4,875,287 A | 10/1989 | Creasy et al. | |
| 4,889,664 A | 12/1989 | Kindt-Larsen | |
| 4,900,552 A | 2/1990 | Sanvordeker et al. | |
| 4,904,247 A | 2/1990 | Therriault et al. | |
| 4,910,015 A | 3/1990 | Sung et al. | |
| 4,925,677 A | 5/1990 | Feijen | |
| 4,942,035 A | 7/1990 | Churchill et al. | |
| 4,942,129 A | 7/1990 | Goosen et al. | |
| 4,948,592 A | 8/1990 | Ayer et al. | |
| 4,959,217 A | 9/1990 | Sanders et al. | |
| 4,961,932 A | 10/1990 | Theeuwes | |
| 4,983,385 A | 1/1991 | Hasegawa et al. | |
| 4,986,987 A | 1/1991 | Ayer et al. | |
| 4,990,582 A | 2/1991 | Salamone | |
| 4,994,081 A | 2/1991 | Civerchia et al. | |
| 5,000,957 A | 3/1991 | Eckenhoff et al. | |
| 5,007,940 A | 4/1991 | Berg | |
| 5,077,336 A | 12/1991 | Nakashita et al. | |
| 5,089,606 A | 2/1992 | Cole et al. | |
| 5,093,130 A | 3/1992 | Fujii et al. | |
| 5,102,676 A | 4/1992 | Aldcroft et al. | |
| 5,112,350 A | 5/1992 | Civerchia et al. | |
| 5,112,618 A | 5/1992 | Cartmell et al. | |
| 5,115,801 A | 5/1992 | Cartmell et al. | |
| 5,116,387 A | 5/1992 | Berg | |
| 5,120,344 A | 6/1992 | Libor | |
| 5,120,544 A | 6/1992 | Henly | |
| 5,134,057 A | 7/1992 | Kuypers et al. | |
| 5,135,297 A | 8/1992 | Valint, Jr. | |
| 5,143,646 A | 9/1992 | Nochumson et al. | |
| 5,147,646 A | 9/1992 | Graham | |
| 5,147,654 A | 9/1992 | Place et al. | |
| 5,154,706 A | 10/1992 | Cartmell et al. | |
| 5,160,328 A | 11/1992 | Cartmell et al. | |
| 5,171,264 A | 12/1992 | Merrill | |
| 5,172,514 A | 12/1992 | Weber et al. | |
| 5,185,152 A | 2/1993 | Peyman | |
| 5,186,936 A | 2/1993 | Groves | |
| 5,192,326 A | 3/1993 | Bao et al. | |
| 5,204,110 A | 4/1993 | Cartmell et al. | |
| 5,212,622 A | 5/1993 | MacFarlane | |
| 5,219,965 A | 6/1993 | Valint, Jr. | |
| 5,232,724 A | 8/1993 | Aldcroft et al. | |
| 5,242,828 A | 9/1993 | Bergstrom et al. | |
| 5,264,214 A | 11/1993 | Rhee et al. | |
| 5,266,325 A | 11/1993 | Kuzma et al. | |
| 5,277,915 A | 1/1994 | Provonchee et al. | |
| 5,284,657 A | 2/1994 | Lu et al. | |
| 5,288,497 A | 2/1994 | Stanley | |
| 5,290,559 A | 3/1994 | Groves | |
| 5,292,514 A | 3/1994 | Capecchi et al. | |
| 5,292,515 A | 3/1994 | Moro et al. | |
| 5,294,446 A | 3/1994 | Schlameus et al. | |
| 5,304,595 A | 4/1994 | Rhee et al. | |
| 5,306,500 A | 4/1994 | Rhee et al. | |
| 5,306,504 A | 4/1994 | Lorenz | |
| 5,314,420 A | 5/1994 | Smith | |
| 5,322,935 A | 6/1994 | Smith | |
| 5,324,775 A | 6/1994 | Rhee et al. | |
| 5,328,955 A | 7/1994 | Rhee et al. | |
| 5,331,059 A | 7/1994 | Engelhardt | |
| 5,336,208 A | 8/1994 | Rosenbluth et al. | |
| 5,336,501 A | 8/1994 | Czech et al. | |
| 5,344,411 A | 9/1994 | Domb et al. | |
| 5,348,973 A | 9/1994 | Raju et al. | |
| 5,364,918 A | 11/1994 | Valint, Jr. et al. | |
| 5,372,766 A | 12/1994 | Roe | |
| 5,378,472 A | 1/1995 | Muzzarelli | |
| 5,382,270 A | 1/1995 | Graham et al. | |
| 5,385,543 A | 1/1995 | Haak et al. | |
| 5,387,415 A | 2/1995 | Wunderlich et al. | |
| 5,399,591 A | 3/1995 | Smith et al. | |
| 5,406,945 A | 4/1995 | Riazzi et al. | |
| 5,409,703 A | 4/1995 | McAnalley et al. | |
| 5,423,736 A | 6/1995 | Cartmell et al. | |
| 5,423,739 A | 6/1995 | Phipps et al. | |
| 5,428,076 A | 6/1995 | Roe | |
| 5,431,921 A | 7/1995 | Thombre | |
| 5,436,066 A | 7/1995 | Chen | |
| 5,436,161 A | 7/1995 | Bergstrom et al. | |
| 5,443,955 A | 8/1995 | Cornell et al. | |
| 5,447,499 A | 9/1995 | Allaire et al. | |
| 5,447,727 A | 9/1995 | Graham | |
| 5,451,406 A | 9/1995 | Lawin et al. | |
| 5,464,629 A | 11/1995 | Monshipouri et al. | |

(56) References Cited

U.S. PATENT DOCUMENTS

| | | |
|---|---|---|
| 5,464,932 A | 11/1995 | Allcock et al. |
| 5,468,505 A | 11/1995 | Hubbell et al. |
| 5,470,911 A | 11/1995 | Rhee et al. |
| 5,474,065 A | 12/1995 | Meathrel et al. |
| 5,482,719 A | 1/1996 | Guillet et al. |
| 5,483,697 A | 1/1996 | Fuchs |
| 5,490,984 A | 2/1996 | Freed |
| 5,492,840 A | 2/1996 | Malmqvist et al. |
| 5,510,418 A | 4/1996 | Rhee et al. |
| 5,512,299 A | 4/1996 | Place et al. |
| 5,512,492 A | 4/1996 | Herron et al. |
| 5,514,379 A | 5/1996 | Weissleder et al. |
| 5,516,532 A | 5/1996 | Atala et al. |
| 5,527,204 A | 6/1996 | Rhoades |
| 5,529,777 A | 6/1996 | Andrianov et al. |
| 5,531,716 A | 7/1996 | Luzio et al. |
| 5,531,999 A | 7/1996 | Cartmell et al. |
| 5,541,304 A | 7/1996 | Thompson |
| 5,543,441 A | 8/1996 | Rhee et al. |
| 5,575,815 A | 11/1996 | Slepian et al. |
| 5,578,307 A | 11/1996 | Wunderlich et al. |
| 5,597,560 A | 1/1997 | Bergamini et al. |
| 5,620,706 A | 4/1997 | Dumitriu et al. |
| 5,622,168 A | 4/1997 | Keusch et al. |
| 5,626,870 A | 5/1997 | Monshipouri et al. |
| 5,633,316 A | 5/1997 | Gartner et al. |
| 5,645,855 A | 7/1997 | Lorenz |
| 5,648,252 A | 7/1997 | Dumitriu et al. |
| 5,656,504 A | 8/1997 | Johansson et al. |
| 5,665,477 A | 9/1997 | Meathrel et al. |
| 5,667,778 A | 9/1997 | Atala |
| 5,677,196 A | 10/1997 | Herron et al. |
| 5,679,058 A | 10/1997 | Rhoades |
| 5,684,051 A | 11/1997 | Thompson |
| 5,684,058 A | 11/1997 | Nunez et al. |
| 5,684,059 A | 11/1997 | Salamone |
| 5,690,981 A | 11/1997 | Watanabe et al. |
| 5,698,213 A | 12/1997 | Jamiolkowski et al. |
| 5,700,289 A | 12/1997 | Breitbart et al. |
| 5,700,583 A | 12/1997 | Jamiolkowski et al. |
| 5,709,854 A | 1/1998 | Griffith-Cima et al. |
| 5,711,960 A | 1/1998 | Shikinami |
| 5,716,404 A | 2/1998 | Vacanti et al. |
| 5,718,862 A | 2/1998 | Thompson |
| 5,718,913 A | 2/1998 | Dhuique-Mayer et al. |
| 5,731,005 A | 3/1998 | Ottoboni et al. |
| 5,733,563 A | 3/1998 | Fortier |
| 5,736,313 A | 4/1998 | Spargo et al. |
| 5,747,570 A | 5/1998 | Date et al. |
| 5,750,585 A | 5/1998 | Park et al. |
| 5,752,974 A | 5/1998 | Rhee et al. |
| 5,762,620 A | 6/1998 | Cartmell et al. |
| 5,763,504 A | 6/1998 | Matsuda et al. |
| 5,766,908 A | 6/1998 | Klein et al. |
| 5,770,712 A | 6/1998 | Roy et al. |
| 5,785,993 A | 7/1998 | Baker et al. |
| 5,791,085 A | 8/1998 | Szmidt et al. |
| 5,792,471 A | 8/1998 | Curatolo |
| 5,792,617 A | 8/1998 | Rotman |
| 5,813,411 A | 9/1998 | Van Bladel et al. |
| 5,820,918 A | 10/1998 | Ronan et al. |
| 5,824,331 A | 10/1998 | Usala |
| 5,834,029 A | 11/1998 | Bellamkonda et al. |
| 5,837,789 A | 11/1998 | Stockhausen et al. |
| 5,838,863 A | 11/1998 | Fujiura et al. |
| 5,843,089 A | 12/1998 | Sahatjian et al. |
| 5,843,156 A | 12/1998 | Slepian et al. |
| 5,846,214 A | 12/1998 | Makuuchi et al. |
| 5,846,842 A | 12/1998 | Herron et al. |
| 5,851,229 A | 12/1998 | Lent et al. |
| 5,858,392 A | 1/1999 | Dumitriu et al. |
| 5,861,023 A | 1/1999 | Vachon |
| 5,869,172 A | 2/1999 | Caldwell |
| 5,874,500 A | 2/1999 | Rhee et al. |
| 5,879,713 A | 3/1999 | Roth et al. |
| 5,887,590 A | 3/1999 | Price |
| 5,888,540 A | 3/1999 | Sugden et al. |
| 5,891,477 A | 4/1999 | Lanza et al. |
| 5,897,874 A | 4/1999 | Stevens et al. |
| 5,900,245 A | 5/1999 | Sawhney et al. |
| 5,902,832 A | 5/1999 | Van Bladel et al. |
| 5,904,927 A | 5/1999 | Amiji |
| 5,906,934 A | 5/1999 | Grande et al. |
| 5,910,519 A | 6/1999 | Nunez et al. |
| 5,919,712 A | 7/1999 | Herron et al. |
| 5,922,352 A | 7/1999 | Chen et al. |
| 5,927,282 A | 7/1999 | Lenker et al. |
| 5,939,208 A | 8/1999 | Stoy |
| 5,942,209 A | 8/1999 | Leavitt et al. |
| 5,955,353 A | 9/1999 | Amiot |
| 5,955,729 A | 9/1999 | Nelson et al. |
| 5,964,644 A | 10/1999 | Rhoades |
| 5,968,556 A | 10/1999 | Atala et al. |
| 5,972,375 A | 10/1999 | Truter et al. |
| 5,973,014 A | 10/1999 | Funk et al. |
| 5,976,526 A | 11/1999 | Atala |
| 5,990,237 A | 11/1999 | Bently et al. |
| 5,994,440 A | 11/1999 | Staples et al. |
| 5,997,301 A | 12/1999 | Linden |
| 5,998,588 A | 12/1999 | Hoffman et al. |
| 6,007,833 A | 12/1999 | Chudzik et al. |
| 6,013,122 A | 1/2000 | Klitzman et al. |
| 6,017,301 A | 1/2000 | Schwartz |
| 6,018,388 A | 1/2000 | Nawacala |
| 6,027,721 A | 2/2000 | Hammang et al. |
| 6,027,744 A | 2/2000 | Vacanti et al. |
| 6,030,635 A | 2/2000 | Gertzman et al. |
| 6,044,201 A | 3/2000 | Van Turnhout |
| 6,045,835 A | 4/2000 | Soper et al. |
| 6,048,337 A | 4/2000 | Svedman |
| 6,051,248 A | 4/2000 | Sawhney et al. |
| 6,060,053 A | 5/2000 | Atala |
| 6,060,534 A | 5/2000 | Ronan et al. |
| 6,063,061 A | 5/2000 | Wallace et al. |
| 6,066,325 A | 5/2000 | Wallace et al. |
| 6,066,613 A | 5/2000 | Tsaur et al. |
| 6,074,660 A | 6/2000 | Jamiolkowski et al. |
| 6,080,412 A | 6/2000 | Jordan et al. |
| 6,087,450 A | 7/2000 | Breitbach et al. |
| 6,106,554 A | 8/2000 | Bretton |
| 6,106,875 A | 8/2000 | Soper et al. |
| 6,110,188 A | 8/2000 | Narciso, Jr. |
| 6,112,908 A | 9/2000 | Michaels |
| 6,113,629 A | 9/2000 | Ken |
| 6,120,807 A | 9/2000 | Gombotz et al. |
| 6,120,904 A | 9/2000 | Hostettler et al. |
| 6,124,273 A | 9/2000 | Drohan et al. |
| 6,126,616 A | 10/2000 | Sanyal |
| 6,129,761 A | 10/2000 | Hubbell |
| 6,132,765 A | 10/2000 | DiCosmo et al. |
| 6,136,873 A | 10/2000 | Hahnle et al. |
| 6,143,821 A | 11/2000 | Houben |
| 6,148,233 A | 11/2000 | Owen et al. |
| 6,153,222 A | 11/2000 | Becher |
| 6,156,572 A | 12/2000 | Bellamkonda et al. |
| 6,162,241 A | 12/2000 | Coury et al. |
| 6,164,012 A | 12/2000 | Lechelt-Kunze et al. |
| 6,171,610 B1 | 1/2001 | Vacanti et al. |
| 6,174,547 B1 | 1/2001 | Dong et al. |
| 6,180,132 B1 | 1/2001 | Huang et al. |
| 6,186,906 B1 | 2/2001 | Sullivan et al. |
| 6,190,603 B1 | 2/2001 | Steinmann et al. |
| 6,193,994 B1 | 2/2001 | Lee et al. |
| 6,200,600 B1 | 3/2001 | Rashid |
| 6,201,065 B1 | 3/2001 | Pathak et al. |
| 6,203,845 B1 | 3/2001 | Qin et al. |
| 6,210,712 B1 | 4/2001 | Edgren et al. |
| 6,214,369 B1 | 4/2001 | Grande et al. |
| 6,217,894 B1 | 4/2001 | Sawhney et al. |
| 6,221,238 B1 | 4/2001 | Grundig et al. |
| 6,224,893 B1 | 5/2001 | Langer et al. |
| 6,224,894 B1 | 5/2001 | Jamiolkowski et al. |
| 6,228,393 B1 | 5/2001 | DiCosmo et al. |
| 6,231,881 B1 | 5/2001 | Usala et al. |

(56) References Cited

U.S. PATENT DOCUMENTS

| | | |
|---|---|---|
| 6,238,403 B1 | 5/2001 | Greene, Jr. et al. |
| 6,245,357 B1 | 6/2001 | Edgran et al. |
| 6,251,823 B1 | 6/2001 | Yamaguchi et al. |
| 6,258,995 B1 | 7/2001 | Gilding et al. |
| 6,264,702 B1 | 7/2001 | Ory et al. |
| 6,268,161 B1 | 7/2001 | Han et al. |
| 6,271,278 B1 | 8/2001 | Park et al. |
| 6,271,345 B1 | 8/2001 | Waldmann et al. |
| 6,274,133 B1 | 8/2001 | Hu et al. |
| 6,274,175 B1 | 8/2001 | Gombotz et al. |
| 6,275,728 B1 | 8/2001 | Venkatraman et al. |
| 6,280,191 B1 | 8/2001 | Gordon |
| 6,281,015 B1 | 8/2001 | Mooney et al. |
| 6,281,319 B1 | 8/2001 | Mentak |
| 6,284,269 B1 | 9/2001 | Struengmann et al. |
| 6,287,588 B1 | 9/2001 | Shih et al. |
| 6,288,154 B1 | 9/2001 | Rhoades |
| 6,303,102 B1 | 10/2001 | Schlichte |
| 6,306,642 B1 | 10/2001 | Nelson et al. |
| 6,309,367 B1 | 10/2001 | Boock |
| 6,319,510 B1 | 11/2001 | Yates |
| 6,320,029 B1 | 11/2001 | Miekka et al. |
| 6,324,703 B1 | 12/2001 | Chen |
| 6,326,018 B1 | 12/2001 | Gertzman et al. |
| 6,333,194 B1 | 12/2001 | Levy et al. |
| 6,339,039 B1 | 1/2002 | Porath et al. |
| 6,340,598 B1 | 1/2002 | Herron et al. |
| 6,348,203 B1 | 2/2002 | Goodman et al. |
| 6,348,212 B2 | 2/2002 | Hymes et al. |
| 6,348,558 B1 | 2/2002 | Harris et al. |
| 6,350,463 B1 | 2/2002 | Herman et al. |
| 6,352,682 B2 | 3/2002 | Leavitt et al. |
| 6,360,129 B1 | 3/2002 | Ley et al. |
| 6,361,629 B2 | 3/2002 | Mahaffy |
| 6,361,790 B1 | 3/2002 | Rolf et al. |
| 6,361,797 B1 | 3/2002 | Kuzma et al. |
| 6,364,893 B1 | 4/2002 | Sahatjian et al. |
| 6,365,185 B1 | 4/2002 | Ritschel |
| 6,368,347 B1 | 4/2002 | Maini et al. |
| 6,372,248 B1 | 4/2002 | Qin et al. |
| 6,379,382 B1 | 4/2002 | Yang |
| 6,383,478 B1 | 5/2002 | Prokop et al. |
| 6,387,978 B2 | 5/2002 | Ronan et al. |
| 6,388,047 B1 | 5/2002 | Won et al. |
| 6,399,091 B1 | 6/2002 | Berthold et al. |
| 6,410,821 B1 | 6/2002 | Roe |
| 6,416,778 B1 | 7/2002 | Ragavan et al. |
| 6,423,332 B1 | 7/2002 | Huxel et al. |
| 6,428,576 B1 | 8/2002 | Haldimann |
| 6,432,449 B1 | 8/2002 | Goldenberg et al. |
| 6,436,441 B1 | 8/2002 | Sako et al. |
| 6,443,980 B1 | 9/2002 | Wang et al. |
| 6,444,217 B1 | 9/2002 | Kwok et al. |
| 6,444,324 B1 | 9/2002 | Yang et al. |
| 6,454,710 B1 | 9/2002 | Ballerstadt et al. |
| 6,455,065 B1 | 9/2002 | Hymes |
| 6,455,600 B1 | 9/2002 | Hahnle et al. |
| 6,458,375 B1 | 10/2002 | Gertzman et al. |
| 6,461,590 B2 | 10/2002 | Spears |
| 6,472,224 B1 | 10/2002 | Wischerhoff et al. |
| 6,475,516 B2 | 11/2002 | DiCosmo et al. |
| 6,475,750 B1 | 11/2002 | Han et al. |
| 6,488,952 B1 | 12/2002 | Kennedy et al. |
| 6,495,488 B2 | 12/2002 | Yamaguchi et al. |
| 6,506,408 B1 | 1/2003 | Palasis |
| 6,514,534 B1 | 2/2003 | Sawhney |
| 6,514,535 B2 | 2/2003 | Marchant |
| 6,514,689 B2 | 2/2003 | Han et al. |
| 6,517,866 B1 | 2/2003 | Am Ende et al. |
| 6,521,243 B2 | 2/2003 | Hassan |
| 6,521,431 B1 | 2/2003 | Kiser et al. |
| 6,524,327 B1 | 2/2003 | Spacek |
| 6,531,152 B1 | 3/2003 | Lerner et al. |
| 6,534,083 B2 | 3/2003 | Gilding et al. |
| 6,541,015 B2 | 4/2003 | Bentley et al. |
| 6,541,020 B1 | 4/2003 | Ding et al. |
| 6,544,287 B1 | 4/2003 | Johnson et al. |
| 6,544,543 B1 | 4/2003 | Mandrusov et al. |
| 6,544,544 B2 | 4/2003 | Hunter et al. |
| 6,544,548 B1 | 4/2003 | Siller-Jackson et al. |
| 6,552,103 B1 | 4/2003 | Bertozzi et al. |
| 6,554,813 B2 | 4/2003 | Kolby-Falk |
| 6,554,857 B1 | 4/2003 | Zilla et al. |
| 6,565,768 B1 | 5/2003 | Dentler et al. |
| 6,579,519 B2 | 6/2003 | Maitra |
| 6,579,978 B1 | 6/2003 | Renier et al. |
| 6,583,219 B2 | 6/2003 | Won |
| 6,585,765 B1 | 7/2003 | Hossainy et al. |
| 6,586,493 B1 | 7/2003 | Massia et al. |
| 6,589,452 B2 | 7/2003 | Asher et al. |
| 6,589,549 B2 | 7/2003 | Shih et al. |
| 6,592,895 B2 | 7/2003 | Lang et al. |
| 6,596,296 B1 | 7/2003 | Nelson et al. |
| 6,596,402 B2 | 7/2003 | Soerens et al. |
| 6,596,763 B1 | 7/2003 | Thormar et al. |
| 6,602,294 B1 | 8/2003 | Sittinger et al. |
| 6,602,671 B1 | 8/2003 | Bawendi et al. |
| 6,602,952 B1 | 8/2003 | Bentley et al. |
| 6,602,975 B2 | 8/2003 | Hubbell et al. |
| 6,605,294 B2 | 8/2003 | Sawhney |
| 6,613,234 B2 | 9/2003 | Voute et al. |
| 6,630,457 B1 | 10/2003 | Aeschlimann et al. |
| 6,632,451 B2 | 10/2003 | Penhasi et al. |
| 6,632,457 B1 | 10/2003 | Sawhney |
| 6,642,363 B1 | 11/2003 | Mooney et al. |
| 6,649,187 B2 | 11/2003 | Hussain et al. |
| 6,652,874 B2 | 11/2003 | Ragavan et al. |
| 6,652,883 B2 | 11/2003 | Goupil et al. |
| 6,656,162 B2 | 12/2003 | Santini, Jr. et al. |
| 6,673,093 B1 | 1/2004 | Sawhney |
| 6,673,108 B2 | 1/2004 | Zilla et al. |
| 6,676,645 B1 | 1/2004 | Bitterhof |
| 6,676,971 B2 | 1/2004 | Goupil et al. |
| 6,681,521 B1 | 1/2004 | Holloway |
| RE38,431 E | 2/2004 | Miekka et al. |
| 6,685,697 B1 | 2/2004 | Arenberg et al. |
| 6,685,745 B2 | 2/2004 | Reever |
| 6,685,962 B2 | 2/2004 | Friedman et al. |
| 6,685,963 B1 | 2/2004 | Taupin et al. |
| 6,686,208 B2 | 2/2004 | Meusel et al. |
| 6,689,165 B2 | 2/2004 | Jacob et al. |
| 6,692,766 B1 | 2/2004 | Rubinstein et al. |
| 6,693,180 B2 | 2/2004 | Lee et al. |
| 6,696,496 B2 | 2/2004 | Oosterbaan et al. |
| 6,699,503 B1 | 3/2004 | Sako et al. |
| 6,699,504 B2 | 3/2004 | Rowe et al. |
| 6,702,983 B2 | 3/2004 | Hu et al. |
| 6,703,044 B1 | 3/2004 | Pinhassi et al. |
| 6,703,047 B2 | 3/2004 | Sawhney et al. |
| 6,706,279 B1 | 3/2004 | Hazzi |
| 6,706,690 B2 | 3/2004 | Reich et al. |
| 6,709,668 B2 | 3/2004 | Won et al. |
| 6,710,126 B1 | 3/2004 | Hirt et al. |
| 6,716,445 B2 | 4/2004 | Won et al. |
| 6,717,015 B2 | 4/2004 | Keltjens et al. |
| 6,723,304 B2 | 4/2004 | Stier |
| 6,723,344 B2 | 4/2004 | Sakiyama-Elbert et al. |
| RE38,522 E | 5/2004 | Gertzman et al. |
| 6,730,298 B2 | 5/2004 | Griffith-Cima et al. |
| 6,730,313 B2 | 5/2004 | Helmus et al. |
| 6,752,826 B2 | 6/2004 | Holloway et al. |
| 6,755,938 B2 | 6/2004 | Kehrer et al. |
| 6,761,895 B2 | 7/2004 | Sawada et al. |
| 6,770,721 B1 | 8/2004 | Kim |
| 6,773,703 B1 | 8/2004 | Ettner et al. |
| 6,773,713 B2 | 8/2004 | Bonassar et al. |
| 6,780,584 B1 | 8/2004 | Edman et al. |
| 6,783,838 B2 | 8/2004 | Coleman et al. |
| 6,793,789 B2 | 9/2004 | Choi et al. |
| 6,793,937 B2 | 9/2004 | Quong |
| 6,800,298 B1 | 10/2004 | Burdick et al. |
| 6,803,420 B2 | 10/2004 | Cleary et al. |
| 6,803,719 B1 | 10/2004 | Miller et al. |
| 6,805,836 B2 | 10/2004 | Salamone et al. |

(56) References Cited

U.S. PATENT DOCUMENTS

| | | |
|---|---|---|
| 6,808,938 B2 | 10/2004 | Hamalainen et al. |
| 6,818,018 B1 | 11/2004 | Sawhney |
| 6,821,331 B2 | 11/2004 | Damodaran |
| 6,824,535 B2 | 11/2004 | Kolby-Falk |
| 6,835,553 B2 | 12/2004 | Han et al. |
| 6,838,053 B2 | 1/2005 | John et al. |
| 6,846,291 B2 | 1/2005 | Smith et al. |
| 6,861,067 B2 | 3/2005 | McGhee et al. |
| 6,863,663 B1 | 3/2005 | Mills et al. |
| 6,867,245 B2 | 3/2005 | Iwata et al. |
| 6,881,420 B2 | 4/2005 | Flashner-Barak et al. |
| 6,884,428 B2 | 4/2005 | Binette et al. |
| 6,888,043 B2 | 5/2005 | Geiser et al. |
| 6,890,339 B2 | 5/2005 | Sahatjian et al. |
| 6,893,466 B2 | 5/2005 | Trieu |
| 6,896,874 B2 | 5/2005 | Li et al. |
| 6,897,072 B1 | 5/2005 | Rich et al. |
| 6,905,700 B2 | 6/2005 | Won et al. |
| 6,911,212 B2 | 6/2005 | Gertzman et al. |
| 6,911,216 B1 | 6/2005 | Roth et al. |
| 6,911,344 B1 | 6/2005 | Reichert et al. |
| 6,913,765 B2 | 7/2005 | Li et al. |
| 6,916,857 B2 | 7/2005 | Won et al. |
| 6,932,974 B2 | 8/2005 | Bezwada et al. |
| 6,939,568 B2 | 9/2005 | Burrell et al. |
| 6,940,580 B2 | 9/2005 | Winterton et al. |
| 6,946,443 B2 | 9/2005 | Blanchat et al. |
| 6,946,499 B2 | 9/2005 | Loomis et al. |
| 6,960,617 B2 | 11/2005 | Omidian et al. |
| 6,964,772 B1 | 11/2005 | Chornet et al. |
| 6,969,451 B2 | 11/2005 | Shin et al. |
| 6,991,652 B2 | 1/2006 | Burg |
| 6,991,804 B2 | 1/2006 | Helmus et al. |
| 6,991,848 B2 | 1/2006 | Thomson |
| 6,992,062 B2 | 1/2006 | Usala |
| 6,997,922 B2 | 2/2006 | Theeuwes et al. |
| 6,998,510 B2 | 2/2006 | Buckman et al. |
| 7,008,567 B2 | 3/2006 | Foulger et al. |
| 7,009,034 B2 | 3/2006 | Pathak et al. |
| 7,014,645 B2 | 3/2006 | Greene, Jr. et al. |
| 7,019,192 B2 | 3/2006 | Gertzman et al. |
| 7,022,343 B2 | 4/2006 | Philbrook et al. |
| 7,025,990 B2 | 4/2006 | Sawhney |
| 7,029,631 B2 | 4/2006 | Leonrad et al. |
| 7,029,697 B2 | 4/2006 | Segura et al. |
| 7,032,251 B2 | 4/2006 | Janssen |
| 7,033,603 B2 | 4/2006 | Nelson et al. |
| 7,041,868 B2 | 5/2006 | Greene et al. |
| 7,045,141 B2 | 5/2006 | Merboth et al. |
| 7,045,366 B2 | 5/2006 | Huang et al. |
| 7,045,559 B2 | 5/2006 | Yahiahaoui et al. |
| 7,049,346 B1 | 5/2006 | Van Bladel et al. |
| 7,052,131 B2 | 5/2006 | McCabe et al. |
| 7,053,150 B2 | 5/2006 | Kozlowski et al. |
| 7,056,957 B2 | 6/2006 | Omidian et al. |
| 7,060,296 B2 | 6/2006 | Hennik et al. |
| 7,064,114 B2 | 6/2006 | Yiv et al. |
| 7,074,175 B2 | 7/2006 | Handy et al. |
| 7,083,806 B2 | 8/2006 | Rippon et al. |
| 7,084,099 B2 | 8/2006 | Radomyselski et al. |
| 7,091,283 B2 | 8/2006 | Muller et al. |
| 7,097,631 B2 | 8/2006 | Trautman et al. |
| 7,097,855 B1 | 8/2006 | Ameer et al. |
| 7,101,621 B2 | 9/2006 | Haddad et al. |
| 7,105,162 B1 | 9/2006 | Schmidt |
| 7,105,182 B2 | 9/2006 | Szymaitis |
| 7,105,352 B2 | 9/2006 | Asher et al. |
| 7,108,860 B2 | 9/2006 | Dueva et al. |
| 7,108,862 B2 | 9/2006 | Remington et al. |
| 7,108,865 B2 | 9/2006 | Curatolo et al. |
| 7,118,761 B2 | 10/2006 | Canada et al. |
| 7,128,929 B1 | 10/2006 | Scherr |
| 7,129,554 B2 | 10/2006 | Lieber et al. |
| 7,138,132 B2 | 11/2006 | Won et al. |
| 7,144,992 B2 | 12/2006 | Madhyastha |
| 7,147,867 B2 | 12/2006 | Dong et al. |
| 7,152,601 B2 | 12/2006 | Barakat et al. |
| 7,153,702 B2 | 12/2006 | Lin et al. |
| 7,156,877 B2 | 1/2007 | Lotz et al. |
| 7,157,428 B2 | 1/2007 | Kusanagi et al. |
| 7,163,920 B2 | 1/2007 | Dhanaraj et al. |
| 7,169,405 B2 | 1/2007 | Trieu |
| 7,172,866 B2 | 2/2007 | Hahn et al. |
| 7,175,430 B1 | 2/2007 | Gasser et al. |
| 7,175,895 B2 | 2/2007 | Janssen |
| 7,176,256 B2 | 2/2007 | Rhee et al. |
| 7,182,783 B2 | 2/2007 | Trieu |
| 7,183,345 B2 | 2/2007 | Kim |
| 7,185,657 B1 | 3/2007 | Johnson et al. |
| 7,186,260 B2 | 3/2007 | Hyson |
| 7,189,414 B2 | 3/2007 | Rubinstein et al. |
| 7,195,778 B2 | 3/2007 | Fleshner-Barak et al. |
| RE39,587 E | 4/2007 | Gertzman et al. |
| 7,205,156 B2 | 4/2007 | Rich et al. |
| 7,211,060 B1 | 5/2007 | Talish et al. |
| 7,211,108 B2 | 5/2007 | Furst et al. |
| 7,217,294 B2 | 5/2007 | Kusanagi et al. |
| 7,217,520 B2 | 5/2007 | Tsinberg et al. |
| 7,220,491 B2 | 5/2007 | Rouns |
| 7,223,282 B1 | 5/2007 | Hossainy |
| 7,238,196 B2 | 7/2007 | Wibaux |
| 7,238,750 B2 | 7/2007 | Muller et al. |
| 7,247,314 B2 | 7/2007 | Hnojewyj et al. |
| 7,252,834 B2 | 8/2007 | Vyavahare et al. |
| 7,261,734 B2 | 8/2007 | Gellman et al. |
| 7,264,527 B2 | 9/2007 | Bawendi et al. |
| 7,267,958 B2 | 9/2007 | Dordick et al. |
| 7,276,246 B2 | 10/2007 | Zhang |
| 7,279,318 B1 | 10/2007 | Seymour et al. |
| 7,279,507 B2 | 10/2007 | Hu et al. |
| 7,303,575 B2 | 12/2007 | Ogle |
| 7,303,814 B2 | 12/2007 | Lamberti et al. |
| 7,309,232 B2 | 12/2007 | Rutherford et al. |
| 7,312,090 B2 | 12/2007 | Lin et al. |
| 7,314,636 B2 | 1/2008 | Caseres et al. |
| 7,320,962 B2 | 1/2008 | Reich et al. |
| 7,328,706 B2 | 2/2008 | Bardach et al. |
| 7,329,414 B2 | 2/2008 | Fisher et al. |
| 7,332,566 B2 | 2/2008 | Pathak et al. |
| 7,342,058 B2 | 3/2008 | Peppmoller et al. |
| 7,351,430 B2 | 4/2008 | St. John et al. |
| 7,364,675 B2 | 4/2008 | Guan et al. |
| 7,364,879 B2 | 4/2008 | Ho et al. |
| 7,371,257 B2 | 5/2008 | Sahatjian et al. |
| 7,371,258 B2 | 5/2008 | Woo et al. |
| 7,374,944 B2 | 5/2008 | Thomson et al. |
| 7,385,101 B2 | 6/2008 | Chandra et al. |
| 7,390,461 B2 | 6/2008 | Grier et al. |
| 7,393,259 B2 | 7/2008 | Heo et al. |
| 7,395,111 B2 | 7/2008 | Levin et al. |
| 7,407,646 B2 | 8/2008 | Laurent et al. |
| 7,407,912 B2 | 8/2008 | Mertens et al. |
| 7,410,651 B2 | 8/2008 | Villa et al. |
| 7,413,739 B2 | 8/2008 | Hubbell et al. |
| 7,413,752 B2 | 8/2008 | Sawhney |
| 7,414,039 B2 | 8/2008 | Parsons |
| 7,415,883 B2 | 8/2008 | Kaplan |
| 7,427,602 B1 | 9/2008 | Shea et al. |
| 7,429,378 B2 | 9/2008 | Serhan et al. |
| 7,431,152 B2 | 10/2008 | Marmo |
| 7,431,943 B1 | 10/2008 | Villa et al. |
| 7,432,069 B2 | 10/2008 | Barman et al. |
| 7,435,452 B2 | 10/2008 | Shimoyama et al. |
| 7,452,868 B2 | 11/2008 | Kuzma et al. |
| 7,455,682 B2 | 11/2008 | Viola |
| 7,462,484 B2 | 12/2008 | Mizuno |
| 7,468,192 B2 | 12/2008 | Mizuno |
| 7,470,420 B2 | 12/2008 | Singaram et al. |
| 7,470,726 B1 | 12/2008 | Kross |
| 7,473,551 B2 | 1/2009 | Warthoe |
| 7,479,229 B2 | 1/2009 | Ho et al. |
| 7,503,936 B2 | 3/2009 | Trieu |
| 7,511,083 B2 | 3/2009 | Madsen et al. |
| 7,517,356 B2 | 4/2009 | Heinrich |

(56) References Cited

U.S. PATENT DOCUMENTS

| | | | |
|---|---|---|---|
| 7,517,856 B2 | 4/2009 | Cohen et al. |
| 7,520,888 B2 | 4/2009 | Trieu |
| 7,520,900 B2 | 4/2009 | Trieu |
| 7,521,064 B2 | 4/2009 | Saxena et al. |
| 7,524,455 B2 | 4/2009 | Potyrailo |
| 7,524,514 B2 | 4/2009 | Brekke |
| 7,531,000 B2 | 5/2009 | Hodorek |
| 7,534,261 B2 | 5/2009 | Friedman |
| 7,547,447 B2 | 6/2009 | Yiu et al. |
| 7,553,903 B2 | 6/2009 | Riegel et al. |
| 7,560,432 B2 | 7/2009 | Kusanagi et al. |
| 7,569,222 B2 | 8/2009 | Woerly |
| 7,569,556 B2 | 8/2009 | Narayan et al. |
| 7,577,470 B2 | 8/2009 | Shah et al. |
| 7,578,846 B2 | 8/2009 | Trieu |
| 7,579,151 B2 | 8/2009 | Lee et al. |
| 7,584,630 B2 | 9/2009 | Van Gemert |
| 7,585,526 B2 | 9/2009 | Hamann |
| 7,592,418 B2 | 9/2009 | Pathak et al. |
| 7,600,378 B2 | 10/2009 | Yeghiazarian et al. |
| 7,605,232 B2 | 10/2009 | Pathak |
| 7,608,101 B2 | 10/2009 | Gellman et al. |
| 7,615,593 B2 | 11/2009 | Kao et al. |
| 7,618,461 B2 | 11/2009 | Trieu |
| 7,620,439 B2 | 11/2009 | Menon et al. |
| 7,622,459 B2 | 11/2009 | Gabrižová |
| 7,629,115 B2 | 12/2009 | Gu et al. |
| 7,629,172 B2 | 12/2009 | Alarcon et al. |
| 7,638,137 B2 | 12/2009 | Chauhan et al. |
| 7,642,240 B2 | 1/2010 | Cohen et al. |
| 7,648,713 B2 | 1/2010 | Sawhney |
| 2002/0193448 A1 | 12/2002 | Wallace et al. |
| 2006/0025815 A1 | 2/2006 | McGurk et al. |
| 2007/0031498 A1 | 2/2007 | Zong et al. |
| 2007/0275246 A1 | 11/2007 | Payne et al. |
| 2008/0187591 A1 | 8/2008 | Rhee et al. |
| 2009/0004276 A1 | 1/2009 | Ben-Shalom et al. |
| 2010/0291055 A1* | 11/2010 | Athanasiadis et al. ....... 424/94.1 |

FOREIGN PATENT DOCUMENTS

| | | |
|---|---|---|
| JP | 2006-524742 | 11/2006 |
| JP | 2008-505709 | 2/2008 |
| WO | WO 03/074099 | 9/2003 |

OTHER PUBLICATIONS

Choi et al. (2002) "Preparation of chitosan oligomers by irradiation" Polymer Degradation and Stability 78:533-538.

* cited by examiner

HYDROGEL COMPOSITIONS

CROSS-REFERENCE TO RELATED APPLICATIONS

This application claims the benefit of U.S. provisional Application No. 61/259,566, filed on Nov. 9, 2009, which is herein incorporated by reference in its entirety.

BACKGROUND OF THE INVENTION

Hydrogels are water-swollen networks of hydrophilic homopolymers or copolymers. These networks may be formed by various techniques; however, the most common synthetic route is the free radical polymerization of vinyl monomers in the presence of a difunctional cross-linking agent and a swelling agent. The resulting polymer exhibits both liquid-like properties, attributable to the major constituent, water, and solid-like properties due to the network formed by the cross-linking reaction. These solid-like properties take the form of a shear modulus that is evident upon deformation.

Hydrogels offer biocompatibility and have been shown to have reduced tendency for inducing thrombosis, encrustation and inflammation when used in medical devices. Unfortunately, the use of hydrogels in biomedical device applications has been hindered by limitations on the form and mechanical characteristics of the existing hydrogels. Many medical devices use hydrogels to improve device biocompatibility; however, many hydrogels can only be used in coatings. Many hydrogels suffer from low modulus, low yield stress, and low strength when compared to non-swollen polymer systems. Lower mechanical properties result from the swollen nature of hydrogels and the non-stress bearing nature of the swelling agent. Existing in situ cured hydrogels provide a benefit in that they can flow to fit a particular tissue, void, or lumen. However, these materials often lose that ability once they cure, and become subject to the drawbacks listed above. Fully cured hydrogels are easier to handle, but lack the shape-filling, conformable characteristics of the in situ curing systems.

Of particular note is that while the biocompatible and conformable characteristics of in situ cured hydrogels are desirable, the methods of applying in situ curing hydrogels are cumbersome. The restriction of keeping two or more reactive components separate from each other and stable during shipment and storage of devices of this type presents a significant burden on the user. Typically, the reactive components are stored apart from any reconstituting fluids in the device kits. At the point of use, the user is required to assemble multiple containers, reconstitute the materials, and transfer the reconstituted materials to a delivery system prior to applying the material. In some cases this process must be completed within a certain time limit to prevent loss of activity of the hydrogel material.

As such, there is a continuing need to develop new compositions capable of forming in situ biocompatible hydrogel structures that offer improved therapeutic outcomes.

RELEVANT LITERATURE

U.S. Pat. Nos. 4,963,489; 5,080,655; 5,250,020; 5,266,480; 5,278,201; 5,278,204; 5,324,775; 5,443,950; 5,599,916; 5,609,629; 5,618,622; 5,652,347; 5,690,955; 5,725,498; 5,741,223; 5,827,937; 5,836,970; 5,852,024; 5,874,417; 5,874,500; 6,071,301; 6,344,272; 6,418,934; 6,428,811; 6,444,797; 6,530,994; 6,551,610; 6,566,406; 6,602,952; 6,645,517; 7,166,574; 7,303,757; 7,414,028; 7,482,427; 7,528,105; and 7,670,592.

U.S. Pat. App. Nos. 2006/0241777, 2007/0196454 and 2007/0231366. and.

Foreign Patent Document No. WO 2009/028965.

Braunova et. al. Collect. Czech. Chem. Commun. 2004, 69: 1643-1656.

Carlson, R. P. et. al. Journal of Polymer Science, Polymer Edition. 2008, 19(8): 1035-1046.

SUMMARY OF THE INVENTION

Fragmented hydrogel compositions and methods of making and using the same are provided. The subject hydrogel compositions are prepared by combining a polymer component and a cross-linking agent followed by a fragmentation process to produce a composition of fragmented hydrogel. Also provided are kits and systems for use in preparing the subject compositions.

These and other objects, advantages, and features of the invention will become apparent to those persons skilled in the art upon reading the details of the disclosure as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
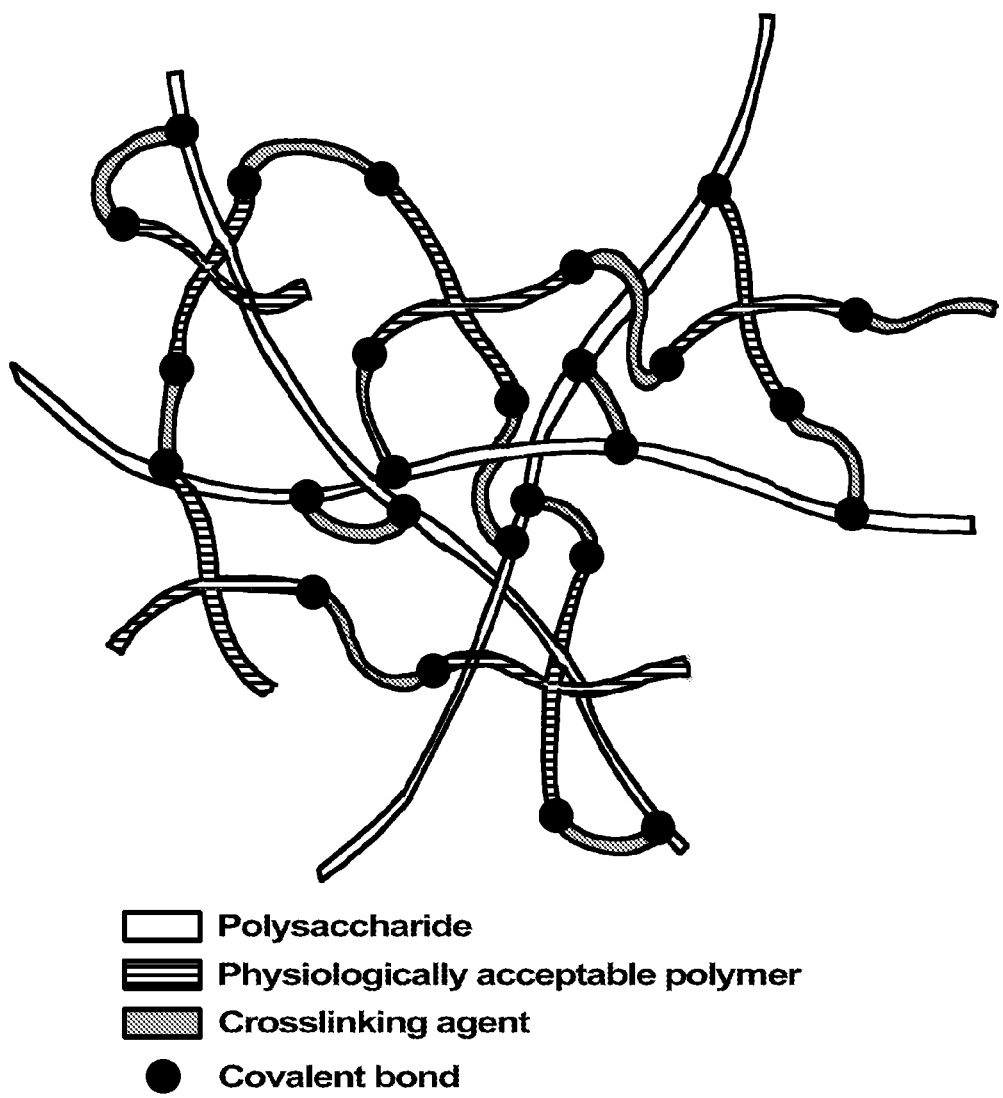
FIG. 1 shows a matrix of an exemplary polysaccharide based hydrogel.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a compound" includes a plurality of such compounds and reference to "the polymer" includes reference to one or more polymer and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

INTRODUCTION

In general, the present invention includes hydrogel compositions that have been fabricated out of a polysaccharide and two or more additional components. The subject hydrogel compositions are characterized by being capable of bonding tissue in both wet (e.g., blood) and dry environments, where adhesion of the composition to the tissue is physiologically acceptable. A further feature of the subject compositions is that they are well tolerated and do not elicit a substantial inflammatory response, if any inflammatory response. The subject compositions can provide multiple desirable qualities such as a combination of any of the following: hemostatic properties, adhesive properties, re-vascularization, biocompatibility, bactericidal, bacteriostatic and/or fungicidal properties, tissue remodeling and/or provides a scaffold for tissue engineering, regeneration, and/or cell seeding, enzymatic or hydrolytic degradation pathways, swelling, engineered residence times, engineered viscosities, temperature or energy activation, inclusion of agents to enable visualization under imaging modalities (X-ray, CT, MRI, US, PET, CTA, etc.), engineered degree of hydrophilicity or hydrophobicity, gap and/or space filling, surface coating, ability to absorb energy, inclusion of foaming agents, inclusion of visual agents, ability to act as a drug delivery platform, media for sound transmission, and engineered durometer. A fragmented hydrogel that is sufficiently hydrated possesses flow properties that are similar to liquid solutions, however, the materials are fully cured and not subject to additional crosslinking reactions once they have been packaged for use. Thus, the fragmented hydrogel of the present invention provides a means to combine the flowable, conformable characteristics of the in situ curing hydrogel formulations with the ease of handling and use of the fully cured hydrogel formulations.

The subject fragmented polysaccharide based hydrogel compositions are prepared by combining or mixing a polysaccharide element and two or more components, such as a polymer and a cross-linking agent. The composition is subsequently fragmented to form small pieces of the polymer matrix that can subsequently be suspended in a solution. An exemplary matrix is provided in FIG. 1. Each of these precursor components or compositions is now reviewed separately in greater detail.

Compositions

As noted above, the compositions of the present invention include a polysaccharide component. Examples of polysaccharides suitable for use with the present invention include, but are not limited to, chitosan, hyaluronic acid, the family of chondroitin sulfates, heparin, keratan sulfate, glycogen, glucose, amylase, amylopectin and derivatives thereof. The polysaccharide may be naturally occurring or synthetically produced. Polysaccharides have several reactive groups that are available for chemical modification. These include the hydroxyl (OH), carboxyl (COOH), and acetamido ($COCH_3$) groups. Further functionality can be imparted to specific polysaccharides in the form of an amine ($NH_2$) group via basic deacetylation, in which a polysaccharide is exposed to basic conditions at elevated temperatures. The degree of deacetylation is dependent on the strength of the alkaline conditions, the temperature of the reaction environment, and the duration of the reaction. For example, the percentage of deacetylation can be controlled to obtain different chitosan molecules from a single source of chitin. Other methods of imparting functionality onto polysaccharides are known to the art, such as the functionalizing of native hyaluronic acid with amine groups through the use of a hydrazide as taught by Prestwich and Marecak in U.S. Pat. No. 5,874,417, which is herein incorporated by reference. In this method, the carboxyl group of the disaccharide is linked to a multi-functional hydrazide under acidic conditions in the presence of a soluble carbodiimide.

In certain embodiments, the polysaccharide is chitosan. Chitosan is a disaccharide formed through the deacetylation of chitin, a naturally occurring material found in crustacean shells and some fungi. Chitosan is a biocompatible, hydrophilic polymer with hemostatic and antimicrobial characteristics. The Chitosan may be from a natural occurring source or may be synthetically synthesized. Chitosan is described in detail is U.S. Pat. Nos. 5,836,970, 5,599,916, and 6,444,797, the disclosures of which are incorporated by reference herein in their entirety.

The non-polysaccharide components of the hydrogel material may include a hydrophilic polymer such as any of the following natural, synthetic, or hybrid polymers: poly(ethylene glycol), poly(ethylene oxide), poly(vinyl alcohol), poly(allyl alcohol), poly(vinylpyrrolidone), poly(alkylene oxides), poly(oxyethylated polyols), poly(ethyleneimine), poly(allylamine), poly(vinyl amine), poly(aminoacids), poly(ethyloxazoline), poly(ethylene oxide)-co-poly(propylene oxide) block copolymers, polysaccharides, carbohydrates, oligopeptides, and polypeptides. The polymer chains may include homo-, co-, or terpolymers of the above materials, in a linear or branched form, and derivatives thereof. These materials may crosslink into a hydrogel through the formation of covalent bonds through the action of chemically active groups that are present on the polysaccharide and the counterpart hydrophilic polymers. Among the chemically active groups that are preferred for use in the present invention are those that can form a covalent bond with the readily available nucleophilic or electrophilic residues.

These exemplary materials may crosslink into a hydrogel through the formation of covalent bonds through the action of chemically active groups that are present on the hydrophilic polymers. Among the chemically active groups that are preferred for use in the present invention are those that can form a covalent bond with the readily available nucleophilic or electrophilic residues.

Examples of electrophilic groups that can react with the nucleophilic groups present on the substrate include but are not limited to carboxyl groups, isocyanates, thiocyanates, N-hydroxysuccinimide esters, glycidyl ethers, glycidyl epoxides, vinyl sulfones, maleimides, orthopyridyl disulfides, iodoacetamides, and carbodiimides. Examples of nucleophilic groups that can react with the electrophilic groups present on the substrate include but are not limited to anhydrides, primary, secondary, tertiary, or quaternary amines, amides, urethanes, ureas, hydrazides, sulfahydryl groups, or thiols. The preceding list of reactive groups serves as an illustrative example; extension to other nucleophilic and electrophilic moieties should be clear to those of skill in the art.

In one embodiment, the hydrogel composition is a three-component hydrogel that includes a multifunctional PEG with terminal nucleophilic groups, a multifunctional PEG with terminal electrophilic groups, and chitosan. When the polymeric components are reconstituted with the appropriate buffers and mixed, they react to form a cohesive hydrogel.

The multifunctional PEG with terminal nucleophilic groups may comprise a difunctionally activated, trifunctionally activated, tetrafunctionally activated, or a star-branched activated polymer. The molecular weight of the multifunctional nucleophilic PEG may be in the range of 1 kiloDalton (kD) to 100 kD; the range of 5 kD to 40 kD; or the range of 10 kD to 20 kD. The multifunctional nucleophilic PEG mass be present in mass percentages of at least 1%; at least 5%; at least 10%; at least 20%; at least 40%; at least 80%; at least 99%.

The multifunctional PEG with terminal electrophilic groups may comprise difunctionally activated, trifunctionally activated, tetrafunctionally activated, or a star-branched activated polymer. The molecular weight of the multifunctional electrophilic PEG may be in the range of 1 kD to 100 kD; the range of 5 kD to 40 kD; or the range of 10 kD to 20 kD. The multifunctional electrophilic PEG mass be present in mass percentages of at least 1%; at least 5%; at least 10%; at least 20%; at least 40%; at least 80%; at least 99%.

The polysaccharide (e.g., chitosan) may be present in a salt or amine form. The chitosan may have a molecular weight in the range of 10 Dalton to 1 kD; the range of 1 kD to 10 kD; the range of 10 kD to 100 kD; the range of 100 kD to 250 kD; the range of 250 kD to 500 kD; or the range of 500 kD to 1000 kD. The chitosan may have a degree of deacetylation in the range of 1% to 10%; the range of 10% to 20%; the range of 20% to 30%; the range of 30% to 40%; the range of 40% to 50%; the range of 50% to 60%; the range of 60% to 70%; the range of 70% to 80%; the range of 80% to 90%; or the range of 90% to 99%. The chitosan may be present in the set hydrogel in a mass percentage range of 0.01% to 0.1%; a range of 0.1% to 0.5%; a range of 0.5% to 1.0%; a range of 1.0% to 5%; a range of 5% to 10%; a range of 10% to 20%; a range of 20% to 40%; a range of 40% to 80%; or a range of 80% to 99%. In certain embodiments, the polysaccharide is chitosan. In further embodiments, the chitosan may also comprise a derivative of chitosan, such as N, O carboxymethylchitosan as described in U.S. Pat. No. 5,888,988, or a dicarboxyl derivatized chitosan as described in WO 2009/028965 the disclosures of which are incorporated herein by reference in their entirety. For example, dicarboxyl derivatized chitosan may be crosslinked to a polyethylene glycol with at least two nucleophilic reactive groups via a polyethylene glycol with at least two electrophilic reactive groups.

An example of a physiologically acceptable polymer that may be suitable for use in this invention is poly(ethylene glycol) that has been modified with a diester to produce a polymer that has a hydrolytically degradable ester linkage in its backbone and a terminal ester group that can be further modified to enable crosslinking with compatible chemical groups. The following examples illustrate the range of hydrolysis rates that a hydrogel comprised of these types of polymers is capable of exhibiting.

Figure 2:
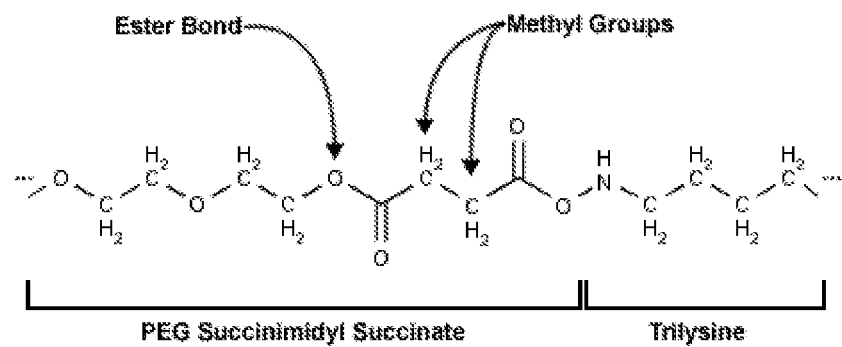
FIG. 2 shows the chemical structure for PEG Succinimidyl Succinate.

Braunova et. al. (Collect. Czech. Chem. Commun. 2004, 69, 1643-1656) have shown that the rate of hydrolysis of ester bonds in poly(ethylene glycol) polymers decreases as the number of methylene groups that border the ester bond is increased. For example, a copolymer of LLL and a multi-armed poly(ethylene glycol) succinimidyl succinate will degrade in approximately 8 days in aqueous media under physiological conditions. As shown in FIG. 2, the succinimidyl succinate has two methyl groups located next to the hydrolytically susceptible ester bond.

Figure 3:
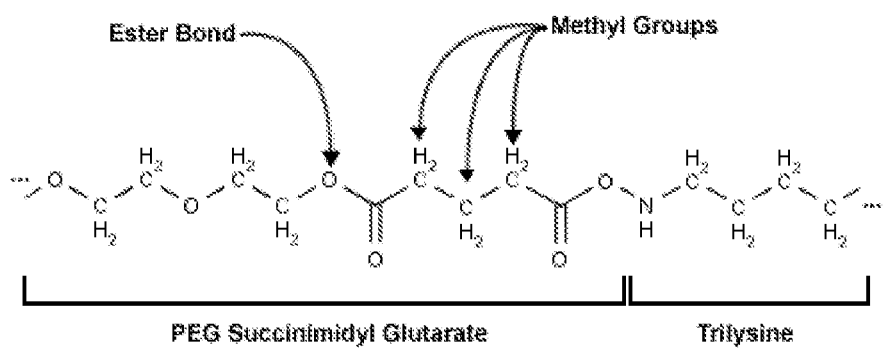
FIG. 3 shows the chemical structure for PEG Succinimidyl Glutarate.

By way of comparison, a copolymer of LLL and a multi-armed poly(ethylene glycol) succinimidyl glutarate will degrade in approximately 50 days in aqueous media under physiological conditions. As shown in FIG. 3, the succinimidyl glutarate has three methyl groups located next to the hydrolytically susceptible ester bond.

As the number of methyl groups neighboring the ester bond increases, the rate of hydrolysis of the ester bond decreases. Further decreases in the rate of hydrolysis of the ester bond should be attained by increasing the number of methyl groups in the PEG polymer along the following progression: PEG succinimidyl adipate, PEG succinimidyl pimelate, PEG succinimidyl suberate, PEG succinimidyl azelate, PEG succinimidyl sebacate, etc. The extension of this method of controlling degradation times to other systems should be readily accessible to one of skill in the art.

The degradation time of the synthetic PEG hydrogels can be also be modified without changing the chemical structure of the underlying polymer components. This situation would arise in the event that a degradation time that is in between the degradation times of two of the polymers listed above. For example, a hydrogel comprised of a 4 armed, 10 kiloDalton, PEG-succinimidyl succinate polymer and trilysine (SS-LLL) degrades in approximately 7 days when exposed to an aqueous medium at 37° C. A hydrogel comprised of a 4 armed, 10 kiloDalton, PEG-succinimidyl glutarate polymer and trilysine (SG-LLL) degrades in approximately 50 days when exposed to an aqueous medium at 37° C. If a hydrogel with a degradation time of approximately 14 days was desired, there are several methods that may be applied to achieve that degradation time using the polymers listed in this example. One method is to fabricate a hydrogel in which the reactive electrophilic groups are provided by a blend of the two PEG polymers and the nucleophilic groups are provided by the trilysine. The stoichiometric blend of the two PEG polymers may be altered to provide the desired degradation time. For example, a blend of PEG polymers in which 65% of the required electrophilic groups are provided by the PEG succinimidyl succinate and 35% of the required electrophilic groups are provide by the PEG succinimidyl glutarate can be combined with trilysine (while maintaining a 1:1 nucleophilic group:electrophilic group stoichiometric ratio) to form a hydrogel that degrades in approximately 14 days when exposed to an aqueous medium at 37° C.

A second method of obtaining an intermediate degradation time would be to vary the stoichiometric ratio of reactive nucleophilic groups to reactive electrophilic groups within the hydrogel precursor polymers. This may be done for hydrogels in which the nucleophilic groups are provided by multiple donors, for hydrogels in which the nucleophilic groups are provided by a single donor, for hydrogels in which the electrophilic groups are provided by multiple donors, for hydrogels in which the electrophilic groups are provided by single donors, or any combination thereof.

A third method of obtaining an intermediate degradation time would be to vary the amount of polymer in the hydrogel. For example, if a given hydrogel contained 5% polymeric content by weight at equilibrium, the degradation time of said hydrogel may be extended by increasing the polymeric content to a value above 5% by weight at equilibrium. Similarly, the degradation time of said hydrogel may be reduced by decreasing the polymeric content to a value below 5% by weight at equilibrium.

A non-degradable formulation may be obtained by using a PEG based polymer that does not degrade under physiological conditions, such as a polymer fabricated from PEG diacrylate or other similar polymers.

Another form of the invention is a three-component hydrogel comprised of a multifunctional PEG with terminal nucleophilic groups, an aldehyde component, and chitosan. When the polymeric components are reconstituted with the appropriate buffers and mixed, they react to form a cohesive hydrogel.

The nucleophilic PEG and polysaccharide (e.g., chitosan) components in the composition are as described earlier. The aldehyde component in the composition as provided herein can be any biocompatible aldehyde with low toxicity. In particular, the aldehyde component includes a di-aldehyde, a polyaldehyde or a mixture thereof. The examples of the aldehyde include, but are not limited to, glyoxal, chondroitin sulfate aldehyde, succinaldehyde, glutaraldehyde, and maleic aldehyde. In some embodiments, the aldehyde component is glutaraldehyde. Other suitable aldehydes which have low toxicity include multifunctional aldehydes derived from naturally-occurring substances, e.g., dextrandialdehyde, or saccharides. The aldehyde component can be an aldehyde product obtained by an oxidative cleavage of carbohydrates and their derivatives with periodate, ozone or the like. The aldehyde may optionally be pre-treated with heat. See U.S. Pat. No. 7,303,757 by Schankereli for "Biocompatible phase invertable proteinaceous compositions and methods for making and using the same", incorporated by reference herein in its entirety. The aldehyde component can be analyzed for properties such as, viscosity, and osmolality. The aldehyde component of an adhesive composition can itself be further comprised of components and/or sub-components. Thus, the aldehyde component can be described in terms of weight, weight-to-weight, weight-to-volume, or volume-to-volume, either before or after mixing. For example, a polysaccharide may be crosslinked to a multifunctional synthetic polymer with at least two reactive nucleophilic groups via a dextran derivatized with aldehyde groups.

In some embodiments, the aldehyde component comprises of about 1-90% aldehyde concentration. In some embodiments, the aldehyde component comprises of about 1-75% aldehyde concentration. In some embodiments, the aldehyde component comprises of about 5-75% aldehyde concentration; about 10-75% aldehyde concentration; about 20-75% aldehyde concentration; about 30-75% aldehyde concentration; about 40-75% aldehyde concentration; about 50-75% aldehyde concentration; or about 60-75% aldehyde concentration.

The composition can comprise at least about 1% aldehyde concentration; at least about 5% aldehyde concentration; at least about 10% aldehyde concentration; at least about 20% aldehyde concentration; at least about 30% aldehyde concentration; at least about 40% aldehyde concentration; at least about 50% aldehyde concentration; at least about 60% aldehyde concentration; at least about 70% aldehyde concentration; at least about 80% aldehyde concentration; at least about 90% aldehyde concentration; or at least about 99% aldehyde concentration. In some embodiments, the adhesive composition comprises of about 1-30%, about 25-75%, about 50-75% or about 75-99% aldehyde concentration.

In some embodiments, the composition comprises of at least about 1% glutaraldehyde concentration; at least about 5% glutaraldehyde concentration; at least about 8% glutaraldehyde concentration; at least about 10% glutaraldehyde concentration; at least about 20% glutaraldehyde concentration; at least about 30% glutaraldehyde concentration; at least about 40% glutaraldehyde concentration; at least about 50% glutaraldehyde concentration; at least about 60% glutaraldehyde concentration; at least about 70% glutaraldehyde concentration; at least about 80% glutaraldehyde concentration; at least about 90% glutaraldehyde concentration; or at least about 99% glutaraldehyde concentration. In some embodiments, the composition comprises about 1-30%, about 25-75%, about 50-75% or about 75-99% glutaraldehyde concentration.

Thickening agents may be added to the forms of the invention described above. The thickening agents include, for example, dextran, carboxymethyl cellulose, polyethylene glycol, liposomes, proliposomes, glycerol, starch, carbohydrates, povidone, polyethylene oxide, and polyvinyl alcohol. In some embodiments, the thickening agent is dextran, polyethylene glycol or carboxymethyl cellulose. In some embodiments, the composition comprises at least about 1% thickening agent concentration; at least about 5% thickening agent concentration; at least about 10% thickening agent concentration; at least about 20% thickening agent concentration; at least about 30% thickening agent concentration; at least about 40% thickening agent concentration; at least about 50% thickening agent concentration; at least about 60% thickening agent concentration; at least about 70% thickening agent concentration; at least about 80% thickening agent concentration; or at least about 90% thickening agent concentration. In some embodiments, the composition comprises at least about 0.5%-10%, at least about 0.5%-25%, or at least about 0.5%-50% thickening agent concentration. In some embodiments, the thickening agent can comprise at least about 0.5% of the composition. The thickening agent can alter a gel time of the composition.

Some embodiments of the aforementioned aspects of the present invention may further comprise a radiopaque material. The radiopaque material includes, for example, bismuth oxide ($Bi_2O_3$), zinc oxide (ZnO), barium sulfate ($BaSO_4$) lanthanum oxide ($La_2O_3$), cerium oxide (CeO2), terbium oxide, ytterbium oxide, neodymium oxide, zirconia ($ZrO_2$), strontia (SrO), tin oxide ($SnO_2$), radiopaque glass and silicate glass. The radiopaque glass includes, for example, barium silicate, silico-alumino barium or strontium containing glass. The silicate glass includes, for example, barium or strontium containing glass. In some embodiments, the radiopaque material comprises at least about 0.001%; at least about 0.05%; at least about 0.1%; at least about 0.2%; at least about 0.5%; at least about 1%; at least about 2%; at least about 5%; at least about 8%; or at least about 10% of the adhesive composition.

The hydrogel compositions as provided herein can optionally contain a variety of naturally occurring or synthetically produced additives such as, but not limited to, water, buffer, saline solution, neutral salt, carbohydrate, fiber, miscellaneous biological material, wetting agent, antibiotics, preservative, dye, thickening agent, thinning agent, fibrinogen, polymer such as polyethylene glycol or combination thereof. Polymers include synthetic polymers such as, polyamides, polyesters, polystyrenes, polyacrylates, vinyl polymers (e.g., polyethylene, polytetrafluoro-ethylene, polypropylene and polyvinyl chloride), polycarbonates, polyurethanes, poly dimethyl siloxanes, cellulose acetates, polymethyl methacrylates, ethylene vinyl acetates, polysulfones, nitrocelluloses and similar copolymers. Polymers further include biological polymers which can be naturally occurring or produced in vitro by fermentation and the like. Biological polymers include, without limitation, collagen, elastin, silk, keratin, gelatin, polyamino acids, polysaccharides (e.g., cellulose and starch) and copolymers thereof.

Flexibilizers can be included in the hydrogel composition to provide flexibility to the material bond upon curing. Flexibilizers may be naturally occurring compositions or synthetically produced. Suitable flexibilizers include synthetic and natural rubbers, synthetic polymers, natural non-native biocompatible proteins (such as exogenous (i.e., non-native) collagen and the like), glycosaminoglycans (GAGs) (such as hyaluronin and chondroitin sulfate), and blood components (such as fibrin, fibrinogen, albumin and other blood factors).

The composition as provided herein can optionally include salts and/or buffers. Examples of the salt include, but are not limited to, sodium chloride, potassium chloride and the like. Suitable buffers can include, for example, ammonium, phosphate, borate, bicarbonate, carbonate, cacodylate, citrate, and other organic buffers such as tris(hydroxymethyl)aminomethane (TRIS), morpholine propanesulphonic acid (MOPS), and N-(2-hydroxyethyl) piperazine-N'(2-ethanesulfonic acid) (HEPES). Suitable buffers can be chosen based on the desired pH range for the hydrogel composition.

Additional additives may be present in the formulation to modify the mechanical properties of the composition. Some additives include, for example, fillers, softening agents and stabilizers. Examples of fillers include, but are not limited to, carbon black, metal oxides, silicates, acrylic resin powder, and various ceramic powders. Examples of softening agents include, but are not limited to, dibutyl phosphate, dioctylphosphate, tricresylphosphate, tributoxyethyl phosphates and other esters. Examples of stabilizers include, but are not limited to, trimethyldihydroquinone, phenyl-β-naphthyl amine, p-isopropoxydiphenylamine, diphenyl-p-phenylene diamine and the like.

One class of additives that may be included in the composition is nanoparticles or nanometer scale constructions. An example of nanoparticles that have been engineered to have specific physical characteristics are nanoshells, as taught by Oldenburg et. al. (U.S. Pat. No. 6,344,272, incorporated herein by reference in its entirety). Nanoshells are comprised of a metallic shell surrounding a non-conducting core; by varying the diameter of the core and the thickness of the shell, the absorption wavelength of the materials can be tuned to specific regions of the spectrum. West et. al. discloses the incorporation of nanoshells into a thermally sensitive polymer matrix for drug delivery in U.S. Pat. Nos. 6,428,811 and 6,645,517, and further teaches the use of nanoshells to treat tumors through localized hyperthermia in U.S. Pat. No. 6,530,994 (the above patents are herein incorporated by reference in their entirety). The combination of nanoparticles or other nanoscale structures with the composition of the invention may provide additional functionality (i.e. tunable absorption spectra) to the composition. In one example, the composition may be employed to fix the nanoparticles tuned to absorb near infrared light in a desired physical position prior to the application of a near-infrared laser to induce local hyperthermia. The incorporation of the nanoshells in the hydrogel matrix prevents the leaching of the nanoshells away from the target area.

The composition may also optionally include a plasticizing agent. The plasticizing agent provides a number of functions, including wetting of a surface, or alternately, increasing the elastic modulus of the material, or further still, aiding in the mixing and application of the material. Numerous plasticizing agents exist, including fatty acids, e.g., oleic acid, palmitic acid, etc., dioctylphtalate, phospholipids, and phosphatidic acid. Because plasticizers are typically water insoluble organic substances and are not readily miscible with water, it is sometimes advantageous to modify their miscibility with water, by pre-mixing the appropriate plasticizer with an alcohol to reduce the surface tension associated with the solution. To this end, any alcohol may be used. In one representative embodiment of this invention, oleic acid is mixed with ethanol to form a 50% (w/w) solution and this solution then is used to plasticize the polymer substrate during the formulation process. Whereas the type and concentration of the plasticizing agent is dependent upon the application, in certain embodiments the final concentration of the plasticizing agent is from about 0.01 to 10% (w/w), including from about 2 to about 4% (w/w). Other plasticizing agents of interest include, but are not limited to: polyethylene glycol, glycerin, butylhydroxytoluene, etc.

Fillers of interest include both reinforcing and non-reinforcing fillers. Reinforcing fillers may be included, such as chopped fibrous silk, polyester, PTFE, NYLON, carbon fibers, polypropylene, polyurethane, glass, etc. Fibers can be modified, e.g., as described above for the other components, as desired, e.g., to increase wettability, mixability, etc. Reinforcing fillers may be present from about 0 to 40%, such as from about 10 to about 30%. Non-reinforcing fillers may also be included, e.g., clay, mica, hydroxyapatite, calcium sulfate, bone chips, etc. Where desired, these fillers may also be modified, e.g., as described above. Non-reinforcing fillers may be present from about 0 to 40%, such as from about 10 to about 30%.

In certain embodiments, the composition may include a foaming agent which, upon combination with the crosslinker composition, results in a foaming composition, e.g., compositions that includes gaseous air bubbles interspersed about. Any convenient foaming agent may be present, where the foaming agent may be an agent that, upon contact with the crosslinking composition, produces a gas that provides bubble generation and, hence, the desired foaming characteristics of the composition. For example, a salt such as sodium bicarbonate in an amount ranging from about 2 to about 5% w/w may be present in the substrate. Upon combination of the substrate with an acidic crosslinker composition, e.g., having a pH of about 5, a foaming composition is produced.

Biologically active agents may be incorporated into the polymer network of the invention; these agents include but are not limited to plasma proteins, hormones, enzymes, antibiotics, antiseptic agents, antineoplastic agents, antifungal agents, antiviral agents, anti-inflammatory agents, growth factors, anesthetics, steroids, cell suspensions, cytotoxins, cell proliferation inhibitors, and biomimetics. The biologically active agents can be incorporated into the hydrogel of the invention by any means known in the art. As a non-limiting example, an agent or multiple agents may be added to the component solutions prior to mixing such that the hydrogel matrix forms around the agent or multiple agents and mechanically encapsulates the agent or agents. Alternatively, the agent or agents may be added to one or all of the component solutions prior to mixing. In another example, the agent or agents may be modified or derivatized to react with the components of the hydrogel and form covalent bonds with the hydrogel. The agent or agents may be bonded to the backbone of the hydrogel structure in a pendent chain configuration or as a fully integrated component of the hydrogel structure. In yet another example, the agent or agents may be suspended within a hydrophobic domain encapsulated within or distributed throughout the hydrogel. Alternatively, the agent or agents may be associated with the backbone of hydrogel through electrostatic, van Der Walls, or hydrophobic interactions. Combinations of any of the aforementioned techniques are also contemplated (e.g. a negatively charged agent that is physically encapsulated in a positively charged hydrogel matrix). The exact means of incorporation will be dictated by the nature of the biologically active agent.

Methods

The hydrogel may be fabricated in a manner suitable to its respective components. For example, a hydrogel comprised of a multi-armed amine-terminated PEG, a chitosan, and a multi-armed ester-terminated PEG may be fabricated by combining the three polymers in a 1:1 functional group molar ratio at a 10% mass fraction in an aqueous basic buffer.

Fragmentation

The term "fragment" refers to a process by which a single, whole, polymeric material is broken into smaller pieces that retain the material properties of the parent material. This may be accomplished by a number of methods, including syringe to syringe mixing of flowable polymer materials, maceration of the polymer material with blades, rotors, hammers, ultrasonic vibrations, or other suitable techniques, filing, sanding, grating, and grinding and/or milling processes, such as cone and gyratory crushing, disk attrition milling, colloid and roll milling, screen milling and granulation, hammer and cage milling, pin and universal milling, jet or fluid energy milling, impact milling and breaking, jaw crushing, roll crushing, disc milling, and vertical rolling, including cryogenic grinding and/or cryogenic milling.

Cryogenic milling or cryogenic grinding refers to a process by which samples are chilled in liquid nitrogen and pulverized to reduce them to a desired particulate size. Cooling samples to approximately −200° C. serves to make flexible samples more brittle and susceptible to grinding. The low temperature also preserves characteristics of the sample that may be lost to the higher temperatures that are present in traditional grinding or milling processes. For example, this can be accomplished by placing the sample in a sealed container along with a magnetically active impactor. The sealed container can then be immersed in a chamber of liquid nitrogen that is surrounded by a magnetic coil. The coil may then be activated once the temperature of the sample reaches approximately −200° C., shuttling the impactor back and forth within the container to pulverize the sample. The size of the particulate can be controlled by varying the length of each grinding session and/or conducting multiple grinding sessions. The sample container may be cooled between grinding sessions to maintain an adequately cool temperature.

Another example of cryogenic milling or grinding uses liquid nitrogen in conjunction with a stirred ball mill. In this method, the sample of interest is loaded into the drum of the stirred ball mill along with grinding media of choice. The type of media may vary according to the desired results of the grinding process (particulate surface area, aspect ratio, shape, compactability, dispersion stability, opacity, flowability, etc.) and the material characteristics of the sample. Typical examples of grinding media include through-hardened steel shot, zirconium silicate, zirconium oxide, flint stones, alumina, silicon nitride, mullite, tungsten carbide, ceramic, chrome steel, glass, silicon carbide, stainless steel, and carbon steel. The size of the grinding media may also vary according to the requirements of the specific grinding process. This listing is not complete, and the identities of additional grinding media should be readily accessible to one of skill in the art. The drum is then sealed and the temperature of the drum is lowered to cryogenic temperatures by flowing liquid nitrogen through a jacket that surrounds the exterior of the drum. Once the contents of the drum have dropped to a sufficient temperature, a shaft running through the center of the drum begins rotating. Arms or discs attached to the shaft agitate the sample and media, pulverizing the sample to the desired size (or alternative specification).

Another cryogenic grinding technique that may be used is to use liquid nitrogen to cool the drum of a conventional ball mill. In this method, the sample and media are loaded into a drum and cooled as described for the stirred ball mill, above. Once a sufficiently depressed drum temperature has been attained, the drum itself is rotated to provide the shear and impact forces necessary for sample fragmentation. Other types of fragmenting that may be amiable to cryogenic processing include, but are not limited to, cone and gyratory crushing, disk attrition milling, colloid and roll milling, screen milling and granulation, hammer and cage milling, pin and universal milling, jet or fluid energy milling, impact milling and breaking, jaw crushing, roll crushing, disc milling, and vertical rolling.

This list does not encompass the entirety of the potential methods of fragmenting a whole polymer into smaller particles. The applicability of other methods should be readily accessible to one of skill in the art.

Drying

The hydrogel may be dried before or after being subjected to fragmentation. The term "drying" refers to any process by which the water content of a candidate polymer material is reduced from an initial value to a lower value. This may be accomplished by placing the material in an environment with lower water content than the polymer material under various temperature and pressure conditions, some of which are listed in Table 1

TABLE 1

| Temperature | Pressure | Example |
| --- | --- | --- |
| Ambient | Ambient | Air drying |
| Elevated | Ambient | Oven drying |
| Ambient | Negative | Vacuum drying |
| Elevated | Negative | Vacuum oven drying |
| Reduced | Negative | Freeze drying |

Application of drying techniques beyond those listed herein should be readily accessible to one of skill in the art. For example, US. Published Pat. App. No. 2007/0231366 teaches a method of drying a hydrogel that comprises halting a solution of components undergoing crosslinking reaction prior to the completion of the reaction by reducing the temperature of the solution below the freezing point of the reacting solution, then subsequently freeze drying the partially-crosslinked hydrogel to remove the solvent from the partially crosslinked hydrogel. The partially crosslinked hydrogel is then processed through a series of treatments that serve to complete the crosslinking reaction. The reliance of this method of fabrication on a phase change between liquid and solid is cumbersome, and places limits on the production methods that can be employed in fabricated hydrogels by the taught method. For example, the timing of the transition of the solution from a liquid to solid state (i.e. freezing) is highly dependent on the physical and material characteristics of the mold (wall thickness, heat transfer coefficient, hydrophilicity or hydrophobicity of the mold surface), the freezing method (cold plate, freezer, immersion in liquid nitrogen, etc.), and the rate of the crosslinking reaction among others. Maintaining a consistent process in the face of these variables is challenging and can provide an obstacle to the scaled-up production of a hydrogel via the taught method.

One method for reducing the complexity of the process taught in US. Published Pat. App. No. 2007/0231366 is to use a method for halting or slowing the rate of the crosslinking reaction that is not subject to as many parameters as freezing, such as changing the pH of the solution of reacting components to a level that does not support further crosslinking. For example, the reaction rate of a second-order nucleophilic substitution between an N-hydroxysuccinimide and a primary amine accelerates as the pH of the reaction media becomes more alkaline and decelerates as the pH of the reaction media becomes more acidic. Therefore, the addition of an aliquot of an acidic solution at a sufficient molarity and volume to shift the pH of the reacting media to an acidic condition will halt or slow the reaction rate of the nucleophilic substitution. Yet another means of changing the rate of reaction is changing the ionic strength of the reaction media. The solution of hydrogel components is then ready for freeze drying. The benefit of this novel method is that the alteration of the reaction rate can be conducted while the hydrogel components are in the liquid phase (e.g. at room temperature), and is not dependent on the size, shape, or material of the casting mold. The independence of the method from the aforementioned limitations will improve consistency of batch-to-batch production lots by reducing the complexity and user-dependence of the process steps and lends itself to scale-up production by simplifying the use of larger molds.

After fragmentation, the resultant collection of polymer particulate may be sorted to achieve a specific distribution of particle sizes. This may be achieved by passing dry polymeric material through a set of sieves, running water soluble polymeric material through a size exclusion column, or other commonly employed sorting techniques.

In one example, the hydrogel is fabricated in an appropriate reaction medium, then dried and fragmented using an appropriate method. The dry particulate can then be loaded into a suitable carrier or delivery device. At the time of use, sterile saline can be introduced to the dry material to rehydrate it into a solution of suspended hydrogel particulate. In a second example, the polymer is fabricated in an appropriate reaction medium, fragmented to a desired size, and dried prior to loading into a suitable carrier or delivery device. Again, sterile saline can be introduced to the dry material at the time of use to rehydrate it into a solution of suspended hydrogel particulate.

Rehydration in Appropriate Media

The process of rehydrating the particulate with an appropriate buffer allows the physical characteristics of the resulting slurry to be controlled. For example, a fragmented hydrogel that is susceptible to hydrolysis under basic conditions may be rehydrated in an acidic aqueous buffer to extend the functional lifetime of the slurry. In another example, the consistency of the slurry may be adjusted from a thick paste to a thin, flowable, liquid by adjusting the mass fraction of dried materials in the reconstituted solution.

In one embodiment of the invention, the polysaccharide and synthetic polymer are dissolved in a neutral or basic buffer. The crosslinker is dissolved in an appropriately pH balanced buffer. The two solutions are combined to allow the formation of a hydrogel network between the polysaccharide, the synthetic polymer, and the crosslinker. The hydrogel is then air-dried to a constant weight and subjected to cryomilling or cryogrinding to produce a collection of particles with a distribution of particle sizes.

In a second embodiment of the invention, the polysaccharide and synthetic polymer are dissolved in a neutral or basic buffer. The crosslinker is dissolved in an appropriately pH balanced buffer. The two solutions are combined to allow the formation of a hydrogel network between the polysaccharide, the synthetic polymer, and the crosslinker. The hydrogel is then fragmented via syringe-to-syringe mixing and stored in the partially-hydrated state. Alternatively, the hydrogel may be placed in an appropriate aqueous media to swell for a specified length of time, or until a specified magnitude of swelling has been attained, prior to fragmenting via syringe-to-syringe mixing. The swelling media may comprise but is not limited to thickening agents, radiopaque agents, preservatives, dyes, thinning agents, flexibilizers, salts and or buffers, fillers, softening agents, stabilizers, nanoparticles, plasticizing agents, biologically active agents, pharmaceutically active agents, and the like.

In a third embodiment of the invention, the polysaccharide and synthetic polymer are dissolved in a neutral or basic buffer. The crosslinker is dissolved in an acidic or neutral buffer along with a steroid or steroids (e.g. triamcinolone, mometasone furoate monohydrate, hydrocortisone, etc.). The two solutions are combined to allow the formation of a hydrogel network between the polysaccharide, the synthetic polymer, and the crosslinker that entraps the steroid or steroids. Steroids are generally insoluble in basic or alkaline solutions, therefore the addition of a steroid to the neutral to acidic buffer containing the crosslinker acts to prevent or mitigate the precipitation of the steroid out of solution prior the incorporation of the steroid into the hydrogel. The hydrogel is then air-dried to a constant weight and subjected to cryomilling or cryogrinding to produce a collection of particles with a distribution of particle sizes that are loaded with the steroid or steroids. The dry particulate is sieved through a series of filters to isolate a desired range of particle sizes, and placed into an aqueous solution at a neutral or acidic pH. The rehydrated slurry may be used in that state to deliver the steroid or steroids to the target anatomy of interest wherein the drug release profile of the steroid is dictated by either the diffusion of the steroid out of the hydrogel, or the hydrolytic or enzymatic degradation of the fragmented hydrogel (in the case of a hydrogel fabricated with hydrolytically and/or enzymatically degradable linkages), or both. The slurry may be further combined with another solution comprising, for example, a thickening agent to result in a viscous solution of steroid-loaded particulate that resists diffusion and/or migration away from the point of delivery.

Alternatively, the polysaccharide and synthetic polymer are dissolved in a neutral or basic buffer. The crosslinker is dissolved in an appropriately pH balanced buffer. The two solutions are combined to allow the formation of a hydrogel network between the polysaccharide, the synthetic polymer, and the crosslinker. The hydrogel is then air-dried to a constant weight and subjected to cryomilling or cryogrinding to produce a collection of particles with a distribution of particle sizes. The dry particulate is sieved through a series of filters to isolate a desired range of particle sizes, and placed into an aqueous solution at a neutral or acidic pH comprising a steroid or steroids to swell. The rehydrated slurry may be used in that state to deliver the steroid or steroids to the target anatomy of interest, or further modified to incorporate additional components including but not limited to radiopaque agents, preservatives, dyes, thinning agents, flexibilizers, salts and or buffers, fillers, softening agents, stabilizers, nanoparticles, plasticizing agents, biologically active agents, pharmaceutically active agents, and the like.

In a fourth embodiment, the polysaccharide and synthetic polymer are dissolved in a neutral or basic buffer. The crosslinker is dissolved in an acidic to neutral buffer along with an anesthetic (e.g. lidocaine, bupivacaine, xylocaine, etc.). The two solutions are combined to allow the formation of a hydrogel network between the polysaccharide, the synthetic polymer, and the crosslinker that entraps the steroid or steroids. Anesthetics are typically formulated in acidic buffers, therefore the addition of an anesthetic to the neutral to acidic buffer containing the crosslinker follows current formulary practice. The hydrogel is then air-dried to a constant weight and subjected to cryomilling or cryogrinding to produce a collection of particles with a distribution of particle sizes that are loaded with the steroid or steroids. The dry particulate is sieved through a series of filters to isolate a desired range of particle sizes, and placed into an aqueous solution at a neutral or acidic pH. The rehydrated slurry may be used in that state to deliver the anesthetic to the target anatomy of interest wherein the drug release profile of the anesthetic is dictated by either the diffusion of the steroid out of the hydrogel, or the hydrolytic or enzymatic degradation of the fragmented hydrogel (in the case of a hydrogel fabricated with hydrolytically and/or enzymatically degradable linkages), or both. The slurry may be further combined with another solution comprising, for example, a thickening agent to result in a viscous solution of an anesthetic-loaded particulate that resists diffusion and/or migration away from the point of delivery.

Alternatively, the polysaccharide and synthetic polymer are dissolved in a neutral or basic buffer. The crosslinker is dissolved in an appropriately pH balanced buffer. The two solutions are combined to allow the formation of a hydrogel network between the polysaccharide, the synthetic polymer, and the crosslinker. The hydrogel is then air-dried to a constant weight and subjected to cryomilling or cryogrinding to produce a collection of particles with a distribution of particle sizes. The dry particulate is sieved through a series of filters to isolate a desired range of particle sizes, and placed into an aqueous solution at a neutral or acidic pH comprising an anesthetic to swell. The rehydrated slurry may be used in that state to deliver the anesthetic to the target anatomy of interest, or further modified to incorporate additional components including but not limited to thickeners, radiopaque agents, preservatives, dyes, thinning agents, flexibilizers, salts and or buffers, fillers, softening agents, stabilizers, nanoparticles, plasticizing agents, biologically active agents, pharmaceutically active agents, and the like.

In a fifth embodiment, the polysaccharide and synthetic polymer are dissolved in a neutral or basic buffer. The crosslinker is dissolved in an acidic to neutral buffer along with an antibiotic (e.g. gentamicin, cephalexin, cefaclore, etc.). The two solutions are combined to allow the formation of a hydrogel network between the polysaccharide, the synthetic polymer, and the crosslinker that entraps the steroid or steroids. Antibiotics are typically formulated in acidic buffers, therefore the addition of an anesthetic to the neutral to acidic buffer containing the crosslinker follows current formulary practice. The hydrogel is then air-dried to a constant weight and subjected to cryomilling or cryogrinding to produce a collection of particles with a distribution of particle sizes that are loaded with the steroid or steroids. The dry particulate is sieved through a series of filters to isolate a desired range of particle sizes, and placed into an aqueous solution at a neutral or acidic pH. The rehydrated slurry may be used in that state to deliver the antibiotic to the target anatomy of interest wherein the drug release profile of the antibiotic is dictated by either the diffusion of the antibiotic out of the hydrogel, or the hydrolytic or enzymatic degradation of the fragmented hydrogel (in the case of a hydrogel fabricated with hydrolytically and/or enzymatically degradable linkages), or both. The slurry may be further combined with another solution comprising, for example, a thickening agent to result in a viscous solution of an antibiotic-loaded particulate that resists diffusion and/or migration away from the point of delivery.

Alternatively, the polysaccharide and synthetic polymer are dissolved in a neutral or basic buffer. The crosslinker is dissolved in an appropriately pH balanced buffer. The two solutions are combined to allow the formation of a hydrogel network between the polysaccharide, the synthetic polymer, and the crosslinker. The hydrogel is then air-dried to a constant weight and subjected to cryomilling or cryogrinding to produce a collection of particles with a distribution of particle sizes. The dry particulate is sieved through a series of filters to isolate a desired range of particle sizes, and placed into an aqueous solution at a neutral or acidic pH comprising an antibiotic to swell. The rehydrated slurry may be used in that state to deliver the antibiotic to the target anatomy of interest, or further modified to incorporate additional components including but not limited to thickeners, radiopaque agents, preservatives, dyes, thinning agents, flexibilizers, salts and or buffers, fillers, softening agents, stabilizers, nanoparticles, plasticizing agents, biologically active agents, pharmaceutically active agents, and the like.

In a sixth embodiment, the polysaccharide and synthetic polymer are dissolved in a neutral or basic buffer. The crosslinker is dissolved in an appropriately pH balanced buffer. The two solutions are combined to allow the formation of a hydrogel network between the polysaccharide, the synthetic polymer, and the crosslinker. The hydrogel is then air-dried to a constant weight and subjected to cryomilling or cryogrinding to produce a collection of particles with a distribution of particle sizes. The dry particulate is sieved through a series of filters to isolate a desired range of particle sizes, and is employed as a carrier for platelet-rich-plasma (PRP). The dry particulate is combined with a solution of PRP to absorb the PRP into the interstices of the hydrogel network. The rehydrated slurry may be used in that state to deliver the PRP to the target anatomy, such as a soft tissue defect (e.g. tendon, ligament, hernia, rotator cuff, etc.), a laceration or external wound bed (e.g. pressure sore, diabetic ulcer, etc.), or a hard tissue defect (e.g. bone) over a specified period of time. Calcium, thrombin or collagen may be added to the rehydrated slurry activate the release of growth factors from the PRP. The slurry may be further modified to incorporate additional components including but not limited to thickeners, radiopaque agents, preservatives, dyes, thinning agents, flexibilizers, salts and or buffers, fillers, softening agents, stabilizers, nanoparticles, plasticizing agents, biologically active agents, pharmaceutically active agents, and the like.

It should be clear that the examples of incorporating the steroid, anesthetic, antibiotic, and PRP into the composition of the invention can be extended to any pharmaceutically or biologically active agent, including but not limited to naturally occurring or synthetically produced plasma proteins, hormones, enzymes, antiseptic agents, antineoplastic agents, antifungal agents, antiviral agents, anti-inflammatory agents, human and non human derived growth factors, anesthetics, cell suspensions, cytotoxins, cell proliferation inhibitors, fibrin, fibrinogen, collagen, and biomimetics.

In a seventh embodiment, the polysaccharide and synthetic polymer are dissolved in a neutral or basic buffer. The crosslinker is dissolved in an appropriately pH balanced buffer. The two solutions are combined to allow the formation of a hydrogel network between the polysaccharide, the synthetic polymer, and the crosslinker. The hydrogel is then vacuum-dried to a constant weight and subjected to cryomilling or cryogrinding to produce a collection of particles with a distribution of particle sizes. The dry particulate is sieved through a series of filters to isolate a desired range of particle sizes and rehydrated in a neutral solution of chitosan to produce a flowable slurry. The viscosity of the slurry can be adjusted by changing the mass percentage of dry particulate or changing the concentration of the chitosan in the rehydrating solution. Alternatively, a second component (e.g. dextran) may be added to the rehydrating solution as a thickening agent. The slurry may be further modified to incorporate additional components including but not limited to radiopaque agents, preservatives, dyes, thinning agents, flexibilizers, salts and or buffers, fillers, softening agents, stabilizers, nanoparticles, plasticizing agents, biologically active agents, pharmaceutically active agents, and the like.

In an eighth embodiment, the polysaccharide and synthetic polymer are dissolved in a neutral or basic buffer. The crosslinker comprises a hydrolytic domain that degrades upon exposure to water, and is dissolved in an acidic buffer. The two solutions are combined to allow the formation of a hydrogel network between the polysaccharide, the synthetic polymer, and the crosslinker. The hydrogel is then vacuum-dried to a constant weight and subjected to cryomilling or cryogrinding to produce a collection of particles with a distribution of particle sizes. The dry particulate is sieved through a series of filters to isolate a desired range of particle sizes and rehydrated in an acidic solution to slow or halt the hydrolysis of the crosslinker and associated degradation of the hydrogel prior to use. The viscosity of the slurry can be adjusted by changing the mass percentage of dry particulate or through the incorporation of a second component (e.g. dextran) as a thickening agent. The slurry may be further modified to incorporate additional components including but not limited to radiopaque agents, preservatives, dyes, thinning agents, flexibilizers, salts and or buffers, fillers, softening agents, stabilizers, nanoparticles, plasticizing agents, biologically active agents, pharmaceutically active agents, and the like.

Utility

The compositions described herein may combine multiple utilities as described below. For example, the hydrogel may be used as an embolic for aneurysmal closure. The composition may be used for the occlusion of neurovascular and/or peripheral aneurysm or the occlusion of Fallopian tubes and/or seminal vesicles for sterilization. Additional applications of the composition on the invention are in varicose vein embolization, uterine fibroid embolization, embolization of hypervascularized tumors, embolization of arterio-venous malformations, meningioma embolization, paraganglioma tumor embolization, and metastatic tumor embolization as taught in U.S. Pat. No. 7,670,592 and herein incorporated by reference in its entirety. The treatment of tumors may or may not include chemotherapeutic agents as a component of the hydrogel.

The composition may be used as a hemostat. One application of the invention is the management of broken, burned, or lacerated mucosal linings, such as the tonsils post tonsillectomy, adenoids post adenoidectomy, after tooth removal, to treat dental dry socket, to treat epistaxis, or treat disruption of any other mucosal surfaces where bleeding control is required. The composition may be used to provide hemostatic control post removal of tissue for biopsy purposes as experienced in liver, lung, kidney, breast, soft tissue, and lymph node biopsies as taught in U.S. Pat. Nos. 5,080,655, 5,741,223, 5,725,498, and 6,071,301. All patents listed in the preceding paragraph are herein incorporated by reference in their entirety.

The composition may be used to act as an agent for the treatment of diabetic foot ulcers, venous stasis ulcers, pressure ulcers, or ulcers and lacerations of any type that require advanced wound management. The purpose of these materials is to provide a moist environment to cover and protect the exposed tissue, and sometimes to stimulate optimal healing as taught in U.S. Pat. Nos. 4,963,489, 5,266,480, and 5,443,950. All patents listed in the preceding paragraph are herein incorporated by reference in their entirety.

The composition may be used as an adhesion barrier in general, gynecologic, and ENT surgical applications to reduce the incidence, extent, and severity of post-operative adhesions. Adhesions are a type of scar tissue that forms a connection between two organs or surfaces that are normally separate in the body. It is hypothesized that the free blood and plasma that result from surgery can form fibrin strands between tissues acutely; these strands can mature within a time span of days into permanent tissue bands which can interfere with normal organ function and lead to other serious clinical complications. They are sometimes associated with endometriosis and pelvic inflammatory disease and are known to frequently form after abdominal, pelvic, or sinus surgery as taught in U.S. Pat. Nos. 5,852,024, 6,551,610, and 5,652,347. Over 90% of patients that undergo surgical procedures of this type may form adhesions. The composition may be formed such that a lumen is maintained in the body of the composition to enable ongoing airflow (i.e. during application following sinus surgery) or drainage of fluids. The composition may also be used as a stent to maintain separation between tissues. In another example, the composition may be used as an ethmoid spacer to maintain an opening into the ethmoid sinuses following surgery. All patents listed in the preceding paragraph are herein incorporated by reference in their entirety.

The compositions described herein may be used as a surface coating on medical devices or tissues to prevent the formation of biofilm, and bacterial or fungal colonies. The selection of a strongly cationic polysaccharide (e.g. Chitosan) as a component of the hydrogel network allows for a continuous surface coating on implants and disposable medical devices that provides a hindrance to biofilm deposition (Carlson, R. P. et. al., Anti-biofilm properties of chitosan coated surfaces. Journal of Polymer Science, Polymer Edition, 19(8): pp 1035-1046, 2008). The mechanism of action may be twofold, the physical structure of the polysaccharide may function disrupt the bacterial cell wall or the cationic nature of the polysaccharide may be exploited to bind with anionic antibiotic agents. Alternatively, a non-polysaccharide component or additive may be used to provide similar antimicrobial, antibacterial, or antifungal properties (e.g., silver). An important application of a surface coated that provides infection control is in the prevention or treatment of osteomyelitis. Osteomyelitis is an infection of bone or bone marrow with a propensity for progression due to pyrogenic bacteria. The presentation of osteomyelitis can be observed due to iatrogenic causes such as joint replacements, internal fixation of fractures, or root canalled teeth. The hydrogel composition of this invention could allow for localized sustained antibiotic therapy. Furthermore, the composition may be designed to prevent or mitigate bacterial or fungal infections, reducing or eliminating the need for prolonged systemic antibiotic therapy as taught in U.S. Pat. Nos. 5,250,020, 5,618,622, 5,609,629, and 5,690,955. All patents listed in the preceding paragraph are herein incorporated by reference in their entirety.

The compositions described herein can be used effectively to form porous and non-porous scaffolds of controlled microstructure favorable to cell seeding and tissue engineering applications. Methods of control of pore size and structure include the following: freeze drying (lyophilization), salt extraction, the use of foaming agents such hydrogen peroxide, and other methods well known in the art. Multiple cell lines are of contemporary interest to enable the growth and repair of complex tissues using these porous and non-porous scaffolds such as vasculature, epithelial tissue, Islet cells for the formation of a tissue engineered pancreas, nerve regeneration, cartilage regeneration and repair, bone growth and repair, and connective and soft tissue repair (ventral and inguinal hernia, pelvic floor reconstruction, vaginal slings, rotator cuffs, tendon, etc.).

The hydrogel composition of this invention may be used in the controlled delivery or administration of therapeutic or palliative agents. The composition may include a synthetic component that acts as a carrier or depot for the therapeutic or palliative agent. The agent may be covalently bound to the structure of the hydrogel matrix or physically entrapped within the hydrogel matrix. The rate of release of the therapeutic or palliative agents may be controlled by modifying the composition of the invention. Targets of contemporary interest include the following: paclitaxel for the treatment of tumors, insulin for the treatment of diabetes, analgesics or anesthetics for the treatment of pain, vasoconstrictors for the control of blood pressure such as amphetamines, antihistamines, pseudo-ephedrine, and caffeine, vasodilators for the control of blood pressure such as alpha blockers, nitric oxide inducers, and papavarine, cholesterol lowering drugs such as statins (e.g. lovostatin), procoagulants for the control of clotting such as protamine sulfate, thrombin, fibrin, and collagen, anticoagulants for the control of clotting such as heparin, coumadin, glycoprotein 2-β-3-α, warfarin, abciximab, and clopidogrel bisulfate, and selective serotonin reuptake inhibitors such as fluoxetine to provide palliative treatment of depression, obsessive/compulsive disorders, bulimia, anorexia, panic disorders, and premenstrual dysphoric disorders, and mono amine oxidase inhibitors such as phenelzine for the palliative treatment of depression. The hydrogel compositions may be used as a carrier for synthetic and human-based bone regrowth agents such as recombinant human bone morphogenic protein as well as biomimetic materials usable for this indication such as B2A, F2A, PBA, LA1, VA5, PBA, LA1, VA5, B7A, F9A, F5A, and F20A from BioSurfaces Engineering Technology, heterodimeric chain synthetic heparin-binding growth factor analogs as taught in U.S. Pat. No. 7,528,105, positive modulator of bone morphogenic protein-2 as taught in U.S. Pat. Nos. 7,482,427 and 7,414,028, growth factor analogs as taught in U.S. Pat. No. 7,414,028, and synthetic heparin-binding growth factor analogs as taught in U.S. Pat. No. 7,166,574, all incorporated herein by reference in their entirety.

The compositions of the current invention have a variety of uses especially in the area of cosmetic surgery and dermatology. Malleable, flowable compositions may be prepared as injectable formulations, and are suitable for superficial to deep dermal augmentation, for example to correct, fill, and support dermal wrinkles, creases, and folds as well as lips as taught in U.S. Pat. Nos. 5,827,937, 5,278,201 and 5,278,204. Larger volume injections can be envisioned for augmentation of breast, penile glans, and other anatomic positions in the body as taught in U.S. Pat. No. 6,418,934; all listed patents are incorporated herein by reference in their entirety. Body sculpting procedures, including breast augmentation, are contemplated for cosmetic and reconstructive purposes. Augmentation of the glans of the penis is used for treatment of premature ejaculation. Historically, the main limitation of medical treatment for premature ejaculation is recurrence after withdrawal of medication. Glans penis augmentation using injectable compositions of the invention facilitate treatment of premature ejaculation via blocking accessibility of tactile stimuli to nerve receptors. The compositions of the invention could also be used as an injectable bulking agent for sphincter augmentation to control incontinence. In this application, the material is injected directly into the sphincter tissue to improve and augment the tissue structure such that sphincter control could be restored. The compositions of the invention may also be used as a filler for breast implants, and as a filler for resorbable implants such as those used for placement against bone and for filling of voids such as between bones as taught in US. Published Pat. App. 2006/0241777 and herein incorporated by reference in their entirety.

The composition described herein may be used as a space filling agent and energy barrier to attenuate existing energy-based procedures and reduce current dose limiting morbidity issues in adjacent tissue. The hydrogel composition of this invention acts as a transient buffer between the non-diseased tissue and the tumor target. The benefits of this approach are twofold; the space filling attribute of the formulation physically moves the collateral tissue away from the target tumor towards which the energy is applied, furthermore, the composition may be formulated to include additives that attenuate the strength of the applied radiation or other energy. For example, the composition may be used to reduce radiation damage of the prostate during radiotherapeutic procedures. The displacement of the tumor away from healthy tissue described herein is also applicable to head and neck cancer, pelvic, thoracic, breast and soft tissue sarcomas. A further use of this composition in radiotherapy and surgical tumor removal procedures is using the composition as a marking system to delineate the boundary of the tumor.

The compositions of the current invention may be used to fill voids in tissue. Potential uses include the treatment of voids in bone, both weight bearing and non-weight bearing, the treatment of voids or gaps in articular cartilage, voids caused by a biopsy procedure, and septal defects of the heart. The treatment of these voids can be enhanced by the inclusion of biologically active agents and biologically activating agents in the hydrogel formulation. For example, recombinant human bone morphogenic protein or allograft human derived bone materials, or demineralized bone matrices, or synthetic biomimetic materials may be incorporated into the composition to aid in the treatment of bone voids.

The compositions of the current environment can be may be used as a synthetic synovial fluid or other type of lubricating agent. By incorporating synthetic polymers that are highly hydrophilic, these materials may find application in fields such as tendon or ligament repair and thoracic surgery. The adhesion of a lacerated tendon that has undergone surgical repair to the tendon sheath reduces the range of motion of the affected digit or limb and increases the work required to attain the range of motion that remains. The deposition of a flowable slurry of the hydrogel composition between the surgically repaired tendon and the tendon sheath may act to reduce friction and enable a lower work of extension for the affected tendon. In thoracic surgery, adhesions may form after thoracic interventions. The introduction of a hydrogel described herein may prevent or reduce the formation of adhesions between the pleura, and in addition, provides a lubricant to movement of the adjacent tissue past each other.

Kits

Also provided are kits for use in practicing the subject methods, where the kits typically include a hydrogel formulation that has been cured prior to shipment to the user. Containers are understood to refer to any structure that may hold or surround the components of the hydrogel composition of the invention; exemplary containers include syringes, vials, pouches, capsules, carpules, ampules, cartridges, and the like. The containers may be shielded from visible, ultraviolet, or infrared radiation through the use of additional components (e.g. a foil pouch surrounding a syringe) or through selection of the material properties of the container itself (e.g. an amber glass vial or opaque syringe).

The subject kits may also include a delivery device (which may or may not include a mixing element), such as a catheter devices (e.g. tubes with one or more lumens of identical or differing sizes and shapes with exit points of varying geometries, dimensions, and positions), syringe(s) of similar or different diameters and volumes, spray elements, check valves, stopcocks, Y-connectors, air bleeder elements (e.g. a membrane that permits the removal of air from a liquid solution prior to delivery to the patient), inlet ports or chambers for the introduction of a forced air stream, disposable cartridges that allow for prolonged deposition of the hydrogel composition, applicators or spreaders, assemblies for realizing a mechanical advantage in delivering the composition of the invention, housings or casings to protect and contain the above mentioned components, and the like.

The kit may further include other components, e.g., desiccants or other means of maintaining control over water content in the kit, oxygen scrubbers or other means of maintaining control over oxygen content within the kit, an inert gas atmosphere (e.g. nitrogen or argon), indicators to convey the maximum temperature experienced by the kit, indicators to convey exposure to sterilizing radiation, ethylene oxide, autoclave conditions, and the like, retaining or positioning structures to prevent damage to the components (e.g. trays or packaging card), that are required to maintain the product in good condition during transport and storage. The following examples are non-limiting and are meant to demonstrate the potential for kitting the hydrogel formulation.

In one embodiment, a container is supplied housing the cured, dried, and fragmented hydrogel formulation. A syringe is supplied containing a buffer appropriate for rehydrating the powder. The syringe is connected to the fragmented hydrogel container and the buffer is introduced to the container to rehydrate the fragmented hydrogel. The rehydrated hydrogel formulation is withdrawn into the syringe, at which point the user can connect it to any of the exemplary device elements previously listed.

In a second embodiment, both the cured, dried, and fragmented hydrogel formulation and the appropriate buffer solution are supplied in a dual chamber syringe. The user rehydrates the dry hydrogel fragments by depressing the syringe plunger and combining the buffer solution with the dry hydrogel fragments. The user can then connect the syringe to any of the exemplary device elements previously listed.

In a third embodiment, the cured, dried and fragmented hydrogel formulation is supplied in a syringe in the rehydrated state. The user can connect the syringe to any of the exemplary device elements that have been previously listed.

In fourth embodiment, the cured, dried and fragmented hydrogel formulation is supplied in a pouch or container for direct application to the target site.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Figure 4:
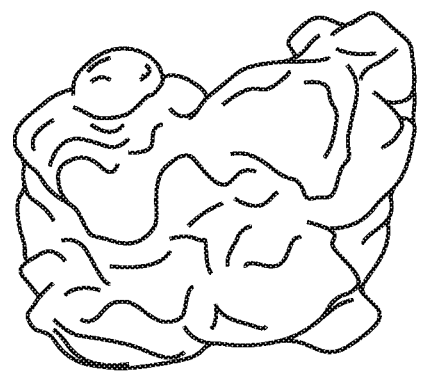
FIG. 4 shows an exemplary composition of a PEG-PEG-Chitosan hydrogel.

A multi-armed polyethylene glycol with amine active groups was combined with chitosan at a 10:1 ratio of polyethylene glycol to chitosan in sodium borate buffer. An equal volume of a multi-armed polyethylene glycol with ester active groups reconstituted in sodium borate buffer at a 2:1 ratio of polyethylene glycol ester to polyethylene glycol amine was mixed with the chitosan solution. After one hour had passed, a firm, clear hydrogel had formed (FIG. 4).

Example 2

Figure 5:
FIG. 5 shows vial of fragmented hydrogel.

The sample of example 1 was dried under ambient temperature and pressure until the water content of the hydrogel had reached equilibrium with the environment (as determined by mass measurement). The sample was subsequently fragmented utilizing a freezer/mill to achieve a finely milled powder (FIG. 5).

Example 3

The dry powder of example 2 was then rehydrated in a saline solution containing a blue-violet dye for purposes of visualization to obtain a slurry of cured, hydrated particles. The slurry was sufficiently flowable to allow extrusion through an 18G needle with minimal pressure.

Example 4

Figure 6:
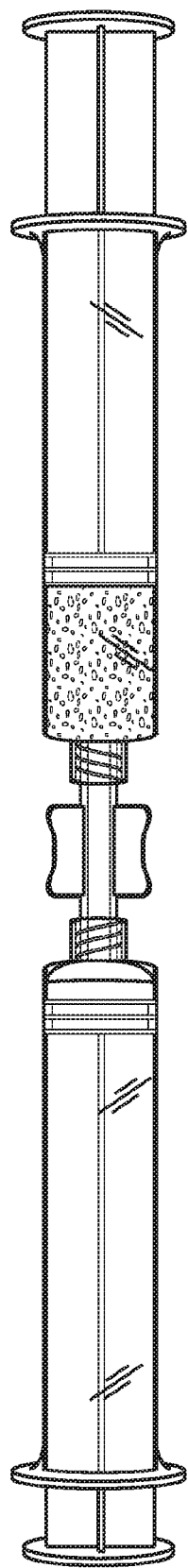
FIG. 6 shows an exemplary syringe configuration for rehydration of fragmented hydrogel.
Figure 7:
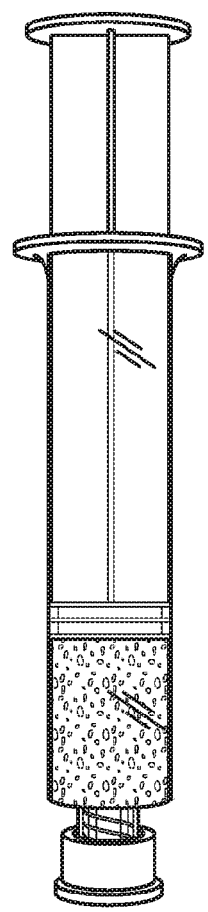
FIG. 7 shows an exemplary composition of rehydrated hydrogel.

A multi-armed polyethylene glycol with amine active groups was combined with chitosan at a 4:1 ratio of polyethylene glycol to chitosan in sodium borate buffer. An equal volume of a multi-armed polyethylene glycol with ester active groups reconstituted in sodium borate buffer at a 2:1 ratio of polyethylene glycol ester to polyethylene glycol amine was mixed with the chitosan solution. After one hour had passed, a firm, clear hydrogel had formed. This sample was sectioned into pieces and loaded into a syringe. A female-female luer connector and a second syringe were connected to the initial syringe to enable syringe to syringe mixing (FIG. 6). A total of 10 passes were performed on the hydrogel formulation, resulting in a slurry that was able to be extruded from an 18G needle (FIG. 7).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A hydrogel composition, comprising
a polysaccharide or derivative thereof having a molecular weight of 1000 Dalton to 80,300 Dalton, a degree of deacetylation of 70% to 99%, and at least two nucleophilic groups, wherein the polysaccharide or derivative thereof is soluble in an aqueous solution;
a multifunctional, multi-armed polyethylene glycol polymer of a molecular weight of 5,000 Dalton to 30,000 Dalton, and comprising at least two nucleophilic groups; and
a multifunctional, multi-armed crosslinker of polyethylene glycol having a molecular weight of 5,000 Dalton to 30,000 Dalton, and comprising at least two electrophilic groups,
wherein the hydrogel composition comprises:
a covalent bond between the polysaccharide or derivative thereof and polyethylene glycol polymer;
a covalent bond between the polysaccharide or derivative thereof and the multi-armed crosslinker; and
a covalent bond between the polyethylene glycol polymer and the multi-armed crosslinker,
wherein the polysaccharide or derivative thereof does not act as a cross-linking agent in the hydrogel.

2. The composition of claim 1, wherein the aqueous solution is alkaline and the polysaccharide is soluble in the aqueous solution up to a concentration of 30 mM.

3. A hydrogel composition, comprising
a chitosan or derivative thereof having a molecular weight of less than or equal to 5,000 Dalton, a degree of deacetylation of 70% to 99%, and at least two nucleophilic groups, wherein the chitosan or derivative thereof is soluble in an aqueous solution;
a multifunctional, multi-armed polyethylene glycol polymer of a molecular weight of 5,000 Dalton to 30,000 Dalton, and comprising at least two nucleophilic groups; and
a multifunctional, multi-armed crosslinker of polyethylene glycol having a molecular weight of 5,000 Dalton to 30,000 Dalton, and comprising at least two electrophilic groups;
wherein the polyethylene glycol polymer comprises ester groups to provide for degradation via hydrolysis and wherein the hydrogel composition comprises:
a covalent bond between the chitosan or derivative thereof and polyethylene glycol polymer;
a covalent bond between the chitosan or derivative thereof and the multi-armed crosslinker; and
a covalent bond between the polyethylene glycol polymer and the multi-armed crosslinker,
wherein the polysaccharide or derivative thereof does not act as a cross-linking agent in the hydrogel.

4. The composition of claim 3, wherein the aqueous solution is alkaline and the chitosan is soluble in the aqueous solution up to a concentration of 30 mM.

5. The composition of claim 1, wherein the polysaccharide substrate is chitosan, carboxymethylcellulose, carboxymethylchitosan or a derivative thereof.

6. The composition of claim 1, wherein the multifunctional, multi-armed crosslinker comprises an aldehyde.

7. The composition of claim 1, wherein the multifunctional, multi-armed crosslinker comprises a glutaraldehyde.

8. The composition of claim 1, wherein the multifunctional, multi-armed crosslinker comprises a heat treated glutaraldehyde.

9. The composition of claim 1, further comprising one or more of a thickening agent, foaming agent, biologically active agent, pharmaceutically active agent, visualization agent and radiopaque agent.

10. The composition of claim 1, wherein the ratio of multifunctional, multi-armed polyethylene glycol polymer to polysaccharide derivative is from 5:1 to 10:1 by mass.

11. The composition of claim 1, wherein the multifunctional, multi-armed polyethylene glycol polymer comprises ester groups to provide for degradation via hydrolysis.

12. The composition of claim 3, wherein the chitosan derivative is carboxymethylchitosan.

13. The composition of claim 3, wherein the multifunctional, multi-armed crosslinker comprises an aldehyde.

14. The composition of claim 3, wherein the multifunctional, multi-armed crosslinker comprises a glutaraldehyde.

15. The composition of claim 3, wherein the multifunctional, multi-armed crosslinker comprises a heat treated glutaraldehyde.

16. The composition of claim 3, further comprising one or more of a thickening agent, foaming agent, biologically active agent, pharmaceutically active agent, visualization agent and radiopaque agent.

17. The composition of claim 3, wherein the ratio of multifunctional, multi-armed polyethylene glycol polymer to polysaccharide derivative is from 5:1 to 10:1 by mass.

18. The composition of claim 3, wherein the multifunctional, multi-armed polyethylene glycol polymer comprises ester groups to provide for degradation via hydrolysis.

* * * * *